(12) United States Patent
Thery et al.

(10) Patent No.: US 9,250,241 B2
(45) Date of Patent: Feb. 2, 2016

(54) USE OF MICROPATTERNED SOFT SUBSTRATE FOR MEASURING OF CELL TRACTION FORCES

(75) Inventors: Manuel Thery, Grenoble (FR); Qingzong Tseng, New Taipei (TW)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 13/984,123

(22) PCT Filed: Feb. 6, 2012

(86) PCT No.: PCT/EP2012/051929
§ 371 (c)(1),
(2), (4) Date: Oct. 2, 2013

(87) PCT Pub. No.: WO2012/107383
PCT Pub. Date: Aug. 16, 2012

(65) Prior Publication Data
US 2014/0024045 A1    Jan. 23, 2014

(30) Foreign Application Priority Data

Feb. 7, 2011    (EP) .................................... 11305123

(51) Int. Cl.
| | | |
|---|---|---|
| G01N 33/567 | (2006.01) | |
| C12M 1/00 | (2006.01) | |
| G01N 33/569 | (2006.01) | |
| G01N 33/50 | (2006.01) | |

(52) U.S. Cl.
CPC ...... *G01N 33/56966* (2013.01); *G01N 33/5026* (2013.01)

(58) Field of Classification Search
CPC ............................. G01N 33/567; C12M 1/00
See application file for complete search history.

(56) References Cited

U.S. PATENT DOCUMENTS

| | | | |
|---|---|---|---|
| 5,108,926 | A | 4/1992 | Klebe |
| 5,470,739 | A | 11/1995 | Akaike et al. |
| 5,976,826 | A | 11/1999 | Singhvi et al. |
| 6,368,838 | B1 | 4/2002 | Singhvi et al. |
| 6,653,089 | B2 | 11/2003 | Takayama et al. |
| 6,893,850 | B2 | 5/2005 | Ostuni et al. |
| 7,288,394 | B2 | 10/2007 | Ostuni et al. |
| 7,955,838 | B2 | 6/2011 | Bornens et al. |
| 8,765,472 | B2 | 7/2014 | Thery |
| 2008/0032403 | A1 | 2/2008 | Saito et al. |
| 2011/0189719 | A1* | 8/2011 | Kuo et al. ..................... 435/29 |
| 2014/0024041 | A1 | 1/2014 | Tseng et al. |

FOREIGN PATENT DOCUMENTS

| | | |
|---|---|---|
| WO | WO 97/07429 | 2/1997 |
| WO | WO 01/70389 | 9/2001 |
| WO | WO 02/22787 | 3/2002 |
| WO | WO 02/086452 | 10/2002 |
| WO | WO 03/080791 A2 | 10/2003 |
| WO | WO 2004/069988 A1 | 8/2004 |
| WO | WO 2005/026313 | 3/2005 |
| WO | WO 2010/011407 | 1/2010 |
| WO | WO 2010/046459 | 4/2010 |
| WO | WO 2012/107445 | 8/2012 |

OTHER PUBLICATIONS

Ghibaudo et al. (Mechanics of cell spreading within 3D-micropatterened environments. Lab Chip (2011) 11, 805-812).*

Jannat et al. (Neutrophil adhesion and chemotaxis depend on substrate mechanics. J. Phys.: Condens. Matter 22:1-14; published Apr. 26, 2010).*

Ghibaudo, M. et al. "Mechanics of cell spreading within 3D-micropatterned environments" *Lab on a Chip*, Jan. 1, 2011, pp. 805-812, vol. 11, No. 5.

Buguin, A. et al. "An array of microfabricated pillars to study cell migration" *M/S Medicine Sciences*, Aug. 1, 2005, pp. 765-767, vol. 21, Nos. 8-9.

Saez, A. et al. "Traction forces exerted by epithelial cell sheets" *Journal of Physics Condensed Matter*, May 19, 2010, pp. 1-9, vol. 22, No. 19.

Du Roure, O. et al. "Force mapping in epithelial cell migration" *PNAS*, Feb. 15, 2005, pp. 2390-2395 and 14122, vol. 102. No. 7.

Tan, J. L. et al. "Cells lying on a bed of microneedles: An approach to isolate mechanical force" *PNAS*, Feb. 18, 2003, pp. 1484-1489, vol. 100, No. 4.

Azioune, A. et al. "Protein Micropatterns: A Direct Printing Protocol Using Deep UVs" *Methods in Cell Biology*, 2010, pp. 133-146, vol. 97.

Thery, M. et al. "Cell Distribution of Stress Fibres in Response to the Geometry of the Adhesive Environment" *Cell Motility and the Cytoskeleton*, 2006, pp. 341-355, vol. 63.

Thery, M. et al. "Anisotropy of cell adhesive microenvironment governs cell internal organization and orientation of polarity" *PNAS*, 2006, Dec. 26, 2006, pp. 19771-19776, vol. 103, No. 52.

Written Opinion in International Application No. PCT/EP2012/051929, Feb. 29, 2012, pp. 1-7.

Marek, L. F. et al. "Organization of the Cytoskeleton in Square Fibroblasts", *Cell Motility*, 1982, pp. 115-130, vol. 2, No. 2.

(Continued)

*Primary Examiner* — Karen Cochrane Carlson
*Assistant Examiner* — Natalie Moss
(74) *Attorney, Agent, or Firm* — Saliwanchik, Lloyd & Eisenschenk

(57) ABSTRACT

The present invention relates to devices and methods for the measurement of cell traction forces. In particular, the invention is based on the use of a soft substrate with cell adhesive micropatterns.

17 Claims, 7 Drawing Sheets

(56) References Cited

OTHER PUBLICATIONS

Grzybowski, B. A. et al. "Generation of Micrometer-Sized Patterns for Microanalytical Applications Using a Laser Direct-Write Method and Microcontact Printing", *Analytical Chemistry*, Nov. 15, 1998, pp. 4645-4652, vol. 70, No. 22.

Branch, D. W. et al. "Long-Term Stability of Grafted Polyethylene Glycol Surfaces for use with Microstamped Substrates in Neuronal Cell Culture", *Biomaterials*, May 2001, pp. 1035-1047, vol. 22, No. 10.

Branch, D. W. et al. "Microstamp Patterns of Biomolecules for High-Resolution Neural Networks", *Medical and Biological Engineering and Computing*, 1998, pp. 135-141, vol. 36, No. 1.

Kam, L. et al. "Correlation of Astroglial Cell Function on Micro-Patterned Surfaces with Specific Geometric Parameters", *Biomaterials*, 1999, pp. 2343-2350, vol. 20, No. 23-24.

Brock, A. et al. "Geometric Determinants of Directional Cell Motility Revealed using Microcontacting Printing", *Langmuir*, 2003, pp. 1611-1617, vol. 19.

Craighead, H. G. et al. "Chemical and topographical patterning for directed cell attachment", *Current Opinion in Solid State and Materials Science*, 2001, pp. 177-184, vol. 5.

Kane, R. S. at al. "Patterning proteins and cells using soft lithography", *Biomaterials*, 1999, pp. 2363-2376, vol. 20.

Lom, B. et al. "A versatile technique for patterning biomolecules onto glass coverslips", *Journal of Neuroscience Methods*, 1993, pp. 385-397, vol. 50.

Nelson, C. M. et al. "Cell-cell signaling by direct contact increases cell proliferation via a PI3K-dependent signal", *FEBS Letters*, 2002, pp. 238-242, vol. 514.

Whitesides, G. M. at al. "Soft Lithography in Biology and Biochemistry", *Annu. Rev. Biomed. Eng.*, 2001, pp. 335-373, vol. 3.

Zhang, S. et al. "Biological surface engineering: a simple system for cell pattern formation", *Biomaterials*, 1999, pp. 1213-1220, vol. 20.

Parker, K. K. at al. "Directional control of lamellipodia extension by constraining cell shape and orienting cell tractional forces", *FASEB J.*, 2002, pp. 1195-1204, vol. 16.

Clark, P. "Cell guidance by micropatterned adhesiveness in vitro", *Journal of Cell Science*, 1992, pp. 287-292, vol. 103.

Nishizawa, M. et al. "Micropatterned HeLa Cell Culture on PEG Monolayer-Coated Glass Substrates", *Chemistry Letters*, 2002, pp. 904-905.

Gopalan, S. et al. "Anisotropic Stretch-Induced Hypertrophy in Neonatal Ventricular Myocytes Micropatterned on Deformable Elastomers" Dec. 23, 2002, *Biotechnology and Bioengineering*, vol. 81, Issue 5, pp. 578-587.

Teixeira, A. et al. "Epithelial contact guidance on well-definied micro- and nanostructured substrates" May 2003, *Journal of Cell Science*, vol. 116, pp. 1881-1892.

Itoga, K. et al. "Cell micropatterning using phoopolymerization with a liquid crystal device commercial projector" Nov. 2003, *Biomaterials 25*, pp. 2047-2053.

Nelson, C. M. et al. "VE-cadherin simultaneously stimulates and inhibits cell proliferation by altering cytoskeletal structure and tension" *Journal of Cell Science*, Sep. 1, 2003, pp. 3571-3581, vol. 116, No. 17.

Huang, S. et al. "Symmetry-Breaking in Mammalian Cell Cohort Migration During Tissue Pattern Formation: Role of Random-Walk Persistance" *Cell Motility and the Cytoskeleton*, Aug. 2005, pp. 201-213, vol. 61, No. 4.

Fink, J. et al. "Comparative study and improvement of current cell micro-patterning techniques" *Lab on a Chip*, Jun. 2007, pp. 672-680, vol. 7, No. 6.

Written Opinion in International Application No. PCT/EP2009/063947, Oct. 23, 2009, pp. 1-9.

Azioune, A. et al. "Simple and rapid process for single cell micropatterning" *Lab on a Chip*, Jan. 1, 2009, pp. 1640-1642, vol. 9, No. 11.

Welle, A. et al. "UV-Based Patterning of Polymeric Substrates for Cell Culture Applications" *Biomedical Microdevices*, Mar. 1, 2002, pp. 33-41, vol. 4, No. 1, Mitchell, S. A. et al. "Cellular attachment and spatial control of cells using micro-patterned ultra-violet/Ozone treatment in serum enriched media" *Biomaterials*, Aug. 1, 2004, pp. 4079-4086, vol. 25, No. 18.

Damljanovic, V. et al. "Bulk and micropatterned conjugation of extracellular matrix proteins to characterized polyacrylamide substrates for cell mechanotransduction assays" *BioTechniques*, Dec. 1, 2005, pp. 847-851, vol. 39, No. 6.

Peterbauer, T. et al. "Simple and versatile methods for the fabrication of arrays of live mammalian cells" *Lab on a Chip*, Jan. 1, 2006, pp. 857-863, vol. 6, No. 7.

Tseng, Q. et al. "A new micropatterning method of soft substrates reveals that different tumorigenic signals can promote or reduce cell contraction levels" *Lap on a Chip*, Jan. 1, 2011, pp. 1-10, vol. 11, No. 13.

Written Opinion in International Application No. PCT/EP2012/052050, Oct. 2, 2012, pp. 1-5.

* cited by examiner

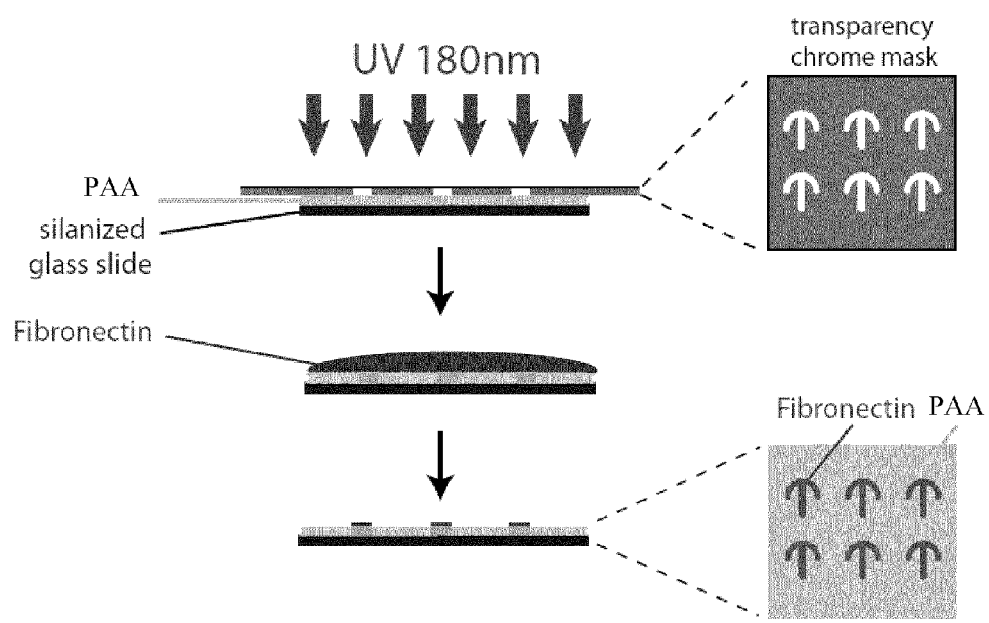
FIGURE 2A
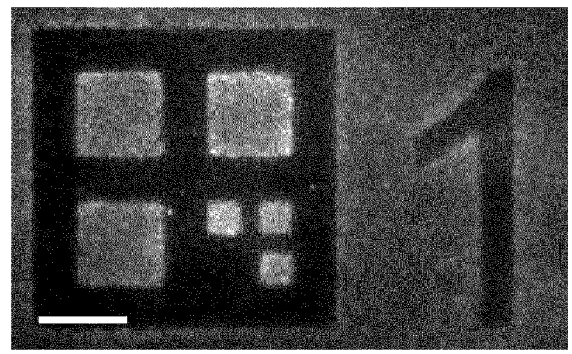
FIGURE 2B
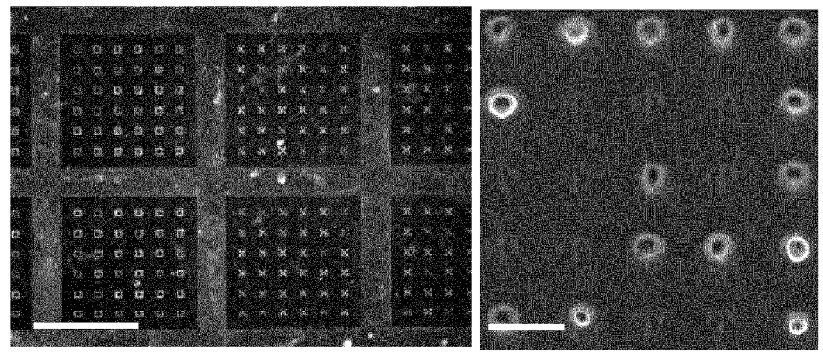
FIGURE 2C      FIGURE 2D

Dose-response

USE OF MICROPATTERNED SOFT SUBSTRATE FOR MEASURING OF CELL TRACTION FORCES

CROSS-REFERENCE TO RELATED APPLICATION

This application is the U.S. national stage application of International Patent Application No. PCT/EP2012/051929, filed Feb. 6, 2012.

FIELD OF THE INVENTION

The present invention relates to a device and method for the measurement of cell traction forces.

BACKGROUND OF THE INVENTION

Tissue homeostasis is highly dependent on cell spatial organization and mechanical balance. Cells attach on their microenvironment and exert traction forces via the myosin dependent contraction of their actin cytoskeleton. The level of cell contraction has recently been shown to have dramatic impact on cell physiology. It directs stem cells differentiation (Engler et al., 2006, Cell 126, 677-689). It also promotes cell growth and has been shown to be responsible for tumoral transformation (Paszek et al., 2005, Cancer Cell 8, 241-254). It is thus necessary to develop reliable and easy to employ methods to measure cell contraction level.

The two main methods to measure cell tractions forces are based on cell culture substrate deformation. They both have limitations in substrate fabrication and force analysis.

Among different methods being developed for force measurement, Traction Force Microscopy (TFM) is one of the most used. However, due to its rather complicate data processing step, this technique still remains exclusive to some specialized groups. Albeit all the materials needed to perform TFM are nearly routine equipments and reagents in ordinary biological laboratory.

The classical TFM proposed by Dembo and Wang (1999, Biophys J 76, 2307-2316) was done on poly-acrylamide (PAA) gel. Basically, PAA gel was prepared with fluorescent micro-beads incorporated inside. Then, the gel was activated by chemical crosslinkers (e.g. Sulfo-SANPAH) and coated homogeneously with extra-cellular matrix (ECM) protein to make the gel available for cell adhesion. When cells attached to the gel, due to the traction force exerted by the cell, the soft substrate deformed and thus the beads displaced. By comparing the image of the displaced beads and another image of the original beads position taken after detaching the cell (e.g., by trypsin treatment), one can obtain the displacement field. The traction force could therefore be obtained by solving a displacement-force inverse problem.

Due to the random positioning of the fiducial marker beads, an image of the relaxed beads position, which can only be obtained after detaching the cell, is always required to obtain the displacement field. This prohibits immediate visualization of cell traction. In addition, tracking of randomly positioned beads between stressed and relaxed images inevitably required manually intervention to correct false bead detection and linking which is rather time consuming. This method requires long numerical calculations and case specific regularizations to deduce the traction force field from the gel deformation field. In addition, PAA gel activation with sulfo-SANPAH is a quite variable step resulting in non homogeneous and non reproducible activation of the substrate. The experimental measure of fluorescent beads displacement is highly sensitive to focus drift (Marganski et al., 2003, Methods Enzymol 361, 197-211). Subsequent defects in automated bead tracking lead to large errors in force measurement (Sabass et al., 2008, Biophys J 94, 207-220).

Errors associated to bead detection could be overcome by using micropatterned dots array on the gel surface (Balaban, 2001, Nat Cell Biol 3, 466-472).

A second method, cell culture on micro-fabricated pillars, allows a much simpler and thus faster force calculation (du Roure et al., 2005, Proc Natl Acad Sci USA 102, 2390-2395; Tan et al., 2003, Proc Natl Acad Sci USA 100, 1484-1489). However the substrate requires several non-trivial microfabrication steps. In addition, micropillars do not support solvent dewetting, and substrate topography can affect cell behavior.

With both techniques, cells can move freely on the substrate. Therefore, they adopt every kind of shapes. This absence of geometrical constraints prevents any automated process for cell force measurement. They are therefore not appropriated for large-scale experiments.

Cell shape control using adhesive micropattern is an efficient method to overcome the above-mentioned limitations. Indeed, adhesive micropatterns coated with ECM allow the normalization of individual cell shape and an accurate control of the spatial distribution of focal adhesion and actin cables (Parker et al., 2002, FASEB J 16, 1195-1204; Thery et al., 2006, Cell Motil Cytoskeleton 63, 341-355; Thery et al., 2006, Proc Natl Acad Sci USA 103, 19771-19776). Appropriate geometries can impose stringent orientation constraints to actin assembly, reduce cell-cell variability and simplify the force calculation method by controlling the location of force application.

Micropatterning on PAA gel has been realized with stencils (Parker et al., 2002, supra; Wang et al., 2002, Cell Motil Cytoskeleton 52, 91-106), or microstructured stamps (Engler et al., 2004, Cell 126, 677-689; Tan et al., 2003, supra) but micropattern resolution is relatively low.

In both cases, micropatterning requires several microfabrication steps, making the whole process long and difficult to realize. In addition, pattern geometries that have been tried so far did not provide accurate control of cell force field.

Extraction of force from displacement data still requires non-trivial calculation. In addition to the non-trivial numerical calculation, cell shape and force distribution were highly variable. This makes large scale quantitative analysis impossible. In particular, the force measurement was still made from displacement of beads, thus suffering from the drawbacks mentioned above. Although the cell shape was controlled, the geometries chosen in their work couldn't regularize traction force distribution. Thus, forces were still randomly distributed, and substrate deformation was complex and differed from one cell to another.

SUMMARY OF THE INVENTION

The main objective of this invention is to simplify, automate and accelerate the traction force measurement by using adhesive micropatterns which can regularize cellular traction forces and at the same time served as the fiducial marker. Complicated force calculation can, therefore, be replaced by a simple measurement of pattern deformation. Traction force measurement thus becomes not only accessible to all biology laboratories, but they also become compatible with high throughput methods and thus could be incorporated in large scale drug screening.

In this invention, the inventors introduce specially designed adhesive micropatterns which can standardize cellular traction force distribution as well as cell shape. Accord-"

ingly, the micropatterns have a form suitable to concentrate the cellular traction force on one single region or point. The micropattern is also fluorescently labeled which allowed a direct and fast readout of traction force by only measuring the deformed pattern image. The relaxed image after detaching the cell is no longer required as well as the problematic beads tracking step and complicate numerical calculation.

The present invention relates to a method for measuring a cellular traction force of one or several cells, comprising:
  providing a soft substrate having disposed thereon an adhesive micropattern having a form suitable to concentrate the cellular traction force on one single region or point;
  exposing the substrate to at least one cell for a period of time sufficient to allow the cell(s) to bind to the adhesive micropattern;
  measuring the position of said single region or point of said micropattern; and
  calculating the displacement of said single region or point of said micropattern, thereby determining the cell traction force.

Preferably, the cellular traction force is determined from a calibration curve showing the relationship between the cellular traction force and the displacement of said single region or point of said micropattern.

The present invention also relates to a device suitable for the above-mentioned method. The device comprises a soft substrate and disposed thereon an adhesive micropattern having a form suitable to concentrate the cellular traction force on one single region or point.

In a preferred embodiment of the method and the device, the adhesive micropattern has a size so as only one individual animal or human cell can adhere on said micropattern.

In a preferred embodiment of the method and the device, the adhesive micropattern includes an adhesive area comprising an adhesive spreading area and two sets of two adhesive spots, wherein:
  a) the adhesive spots are on or close to the convex envelope of the adhesive micropattern;
  b) each set contains a spot on either side of an axis in the plane of the convex envelope;
  c) the two spots located on same side of the axis are separated by a non-adhesive region forming between 15% and 35% of the total length of the convex envelope;
  d) the first set of adhesive spots are essentially located close to or on the axis in order to form an adhesive region of no more than 10% of the total length of the convex envelope; and
  e) the adhesive spreading area is disposed on each side of the axis between the second set of adhesive spots to connect the two spots and toward the first set of adhesive spots between the two non-adhesive regions of c).

Preferably, the micropattern is one micropattern as defined in FIG. 1B. More preferably, the adhesive micropattern may have a shape of crossbow. More preferably, the single region or point is labelled, preferably labelled by fluorescence. Still more preferably, the adhesive micropattern is labelled, preferably labelled by fluorescence.

In a preferred embodiment of the method and the device, the substrate comprises several adhesive micropatterns, identical or different.

In a preferred embodiment of the method and the device, the soft substrate has a Young's modulus of about 1 to about 10 kPa. In another embodiment, the soft substrate is a polyacrylamide gel. More preferably, the soft substrate is a polyacrylamide gel and has a Young's modulus of about 1 to about 10 kPa.

The present invention also relates to a kit for measuring a cellular traction force of a cell, said kit comprising a device as disclosed herein and a calibration curve showing the relation between the cellular traction force and the displacement of the single region or point of the micropattern.

The present invention further relates to the use of a device as disclosed herein for measuring a cellular traction force of a cell.

The present invention relates to a method for determining the effect of a candidate/test molecule on the traction force of a cell, comprising:
  measuring the traction force of a cell by the method as defined above;
  measuring the traction force of the cell incubating with the candidate/test molecule by the method as defined above; and,
  comparing the traction force of the cell incubating or not with the candidate/test molecule, thereby determining the effect of the candidate/test molecule on the traction force of the cell.

The present invention also relates to a method for determining the difference of cellular traction of two types of cells, comprising:
  measuring the traction force of a first type of cells by the method as defined above;
  measuring the traction force of a second type of cells by the method as defined above; and
  comparing the traction force of the first and second types of cells, thereby determining the difference of cellular traction of the two types of cells.

BRIEF DESCRIPTION OF THE DRAWINGS

FIG. 1—Schematic representation of the adhesive micropatterns

FIG. 1C: Adhesive spots are too far away from each other. Cell won't spread on all of them and won't pull on the bottom spot.

FIG. 1D: There is no non-adhesive edge to stimulate and position traction forces.

FIG. 1E: There is only one non-adhesive edge. Traction forces will not be fully stimulated. They will also not be focused on one single point.

FIG. 1F: The two non-adhesive edges are too short. Traction forces will not be fully stimulated.

FIG. 1G: The two non-adhesive edges are too far away from each other. Traction forces will not be focused on one single point.

FIG. 2—Micropatterning of PAA gel.

FIG. 2A: PAA micropatterning method. The gel is polymerized on the photomask, exposed to deep UV and coated with ECM proteins. Cells attach specifically to the UV exposed regions.

FIG. 2B: Fibronectin and fibrinogen-A546 coating on micropatterned PAA. Scale bar represents 10 μm.

FIG. 2C: Fibronectin and fibrinogen-A546 coating on micropatterned PAA. Scale bar represents 500 μm.

FIG. 2D: MCF10A cells (phase contrast) plated on crossbow shaped micropattern (red) on PAA. Cells specifically attach and on micropatterns. Scale bar represents 100 μm.

FIG. 3—Actin cytoskeleton streamlining normalizes cell traction force field.

Scale bar is 10 μm. Traction magnitude is given in Pascals.

FIG. 4—Simple measurement of micropattern deformation allows easy, fast and accurate force quantification.

Figure 4A:
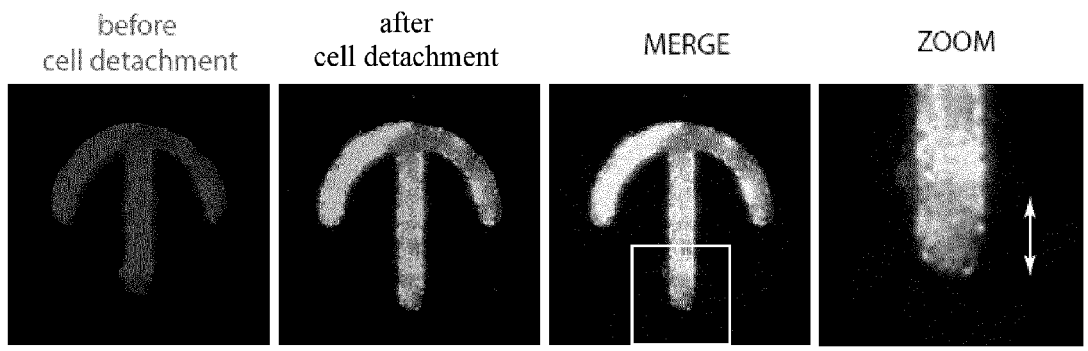

FIG. 4A: Fibrinogen-Alexa 546 coating was used to measure micropattern deformation. Pictures of micropatterns were taken before and after cell detachment with trypsin to visualize micropattern deformation upon cell traction forces.

Figure 4B:
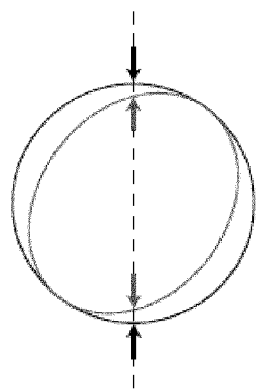
Figure 4B:
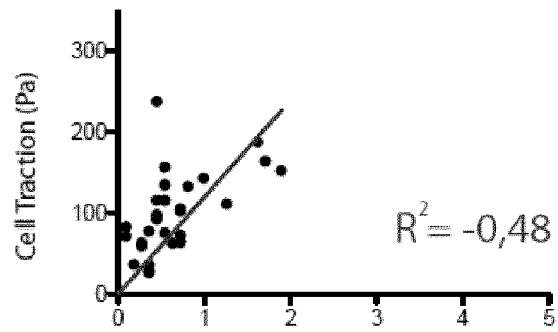

FIG. 4B: Drawings represent micropattern shape before and after cell detachment. The micropattern deformation length corresponded to the distance between the two arrows. Micropattern deformation was then plotted against the total traction force exerted by the cell. Data points were fitted with a linear regression (full line). On discs, micropattern deformation could not be predicted. It was measured along an arbitrary vertical axis. The correlation in this case between total traction and micropattern deformation was not good.

Figure 4C:
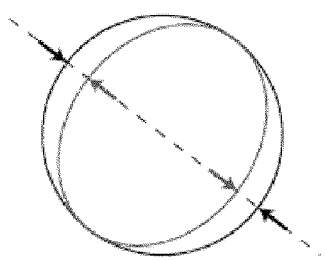
Figure 4C:
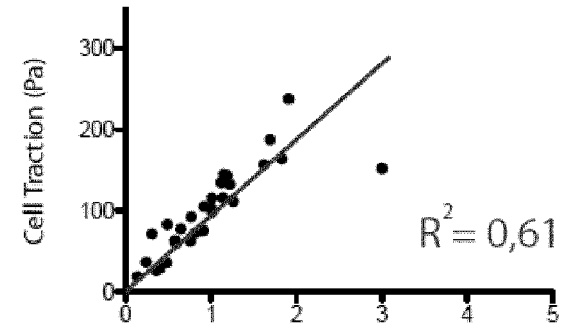

FIG. 4C: When disc deformation was measured along the axis displaying the largest deformation, the correlation was better.

Figure 4D:
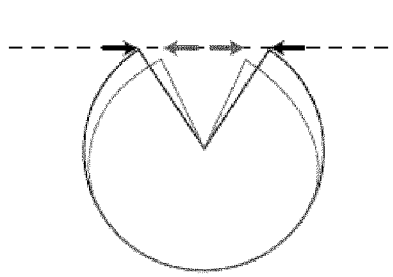
Figure 4D:
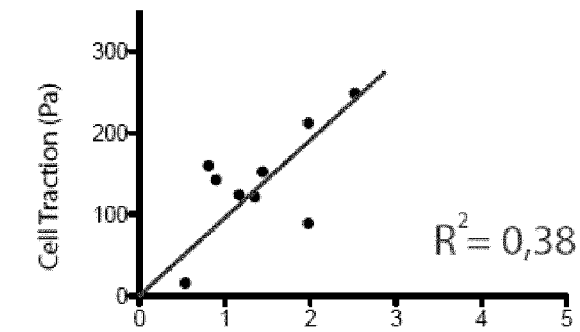

FIG. 4D: On pacman shaped micropatterns the correlation was not good since the deformation was quite small and associated to large errors.

Figure 4E:
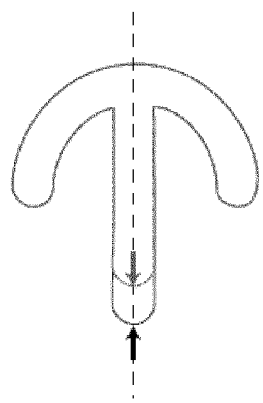
Figure 4E:
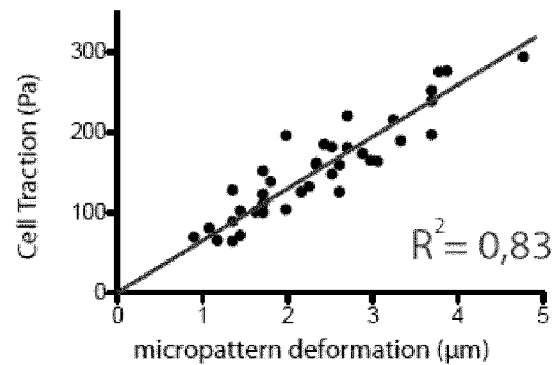

FIG. 4E: On crossbow shaped micropatterns cell total traction force could be directly correlated to micropattern deformation with a small deviation from the linear fit. This calibration curve was used in the following experiments.

Figure 4F:
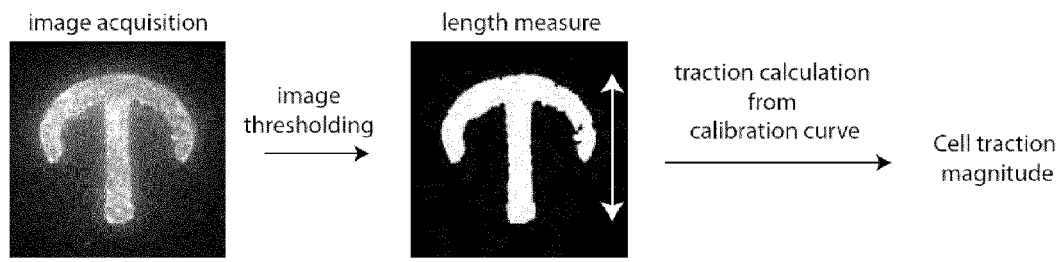

FIG. 4F: New methodology to measure cell traction forces without bead displacement measurements or inverse problem calculation.

FIG. 5—Applications of large-scale force measurements to tumoral transformation analysis.

Figure 5A:
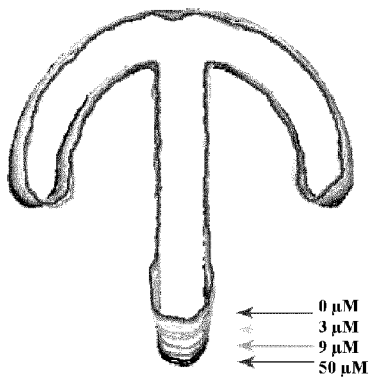
Figure 5A:
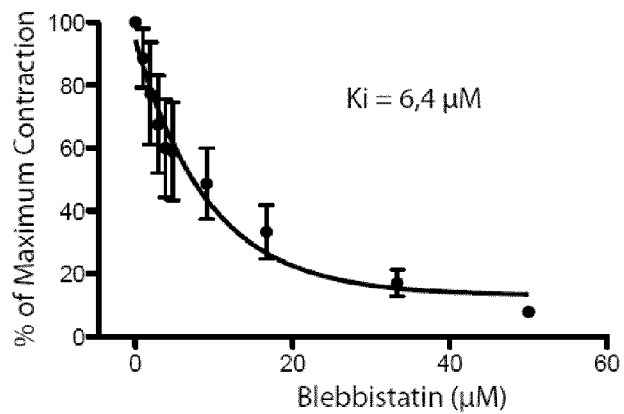

FIG. 5A: Cell traction forces in response to Blebbistatin calculated with method illustrated in FIG. 4F. Increasing drug concentrations were successively applied to 6 cells. Micropattern contours show a representative micropattern relaxation upon increasing drug concentrations. In the graph, cell maximal tractions in the absence of Blebbistatin were renormalized. Error bars represent the standard deviation. Data were fitted with a single exponential decay (full line) to calculate the IC50, i.e., drug concentration for half effect.

Figure 5B:
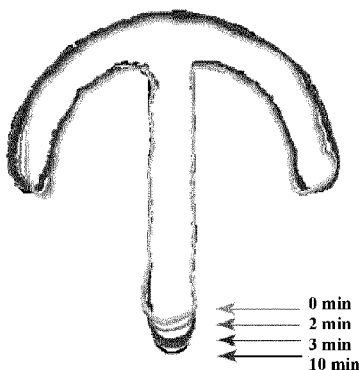
Figure 5B:
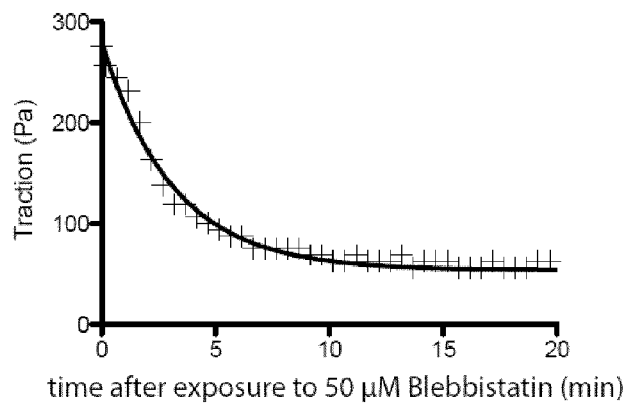

FIG. 5B: Cell traction forces over time in response to 50 μM of Blebbistatin calculated with method illustrated in FIG. 4F. Micropattern contours show a representative micropattern relaxation over time. Measurements were performed on a single cell. Data were fitted with a single exponential decay (full line).

Figure 5C:
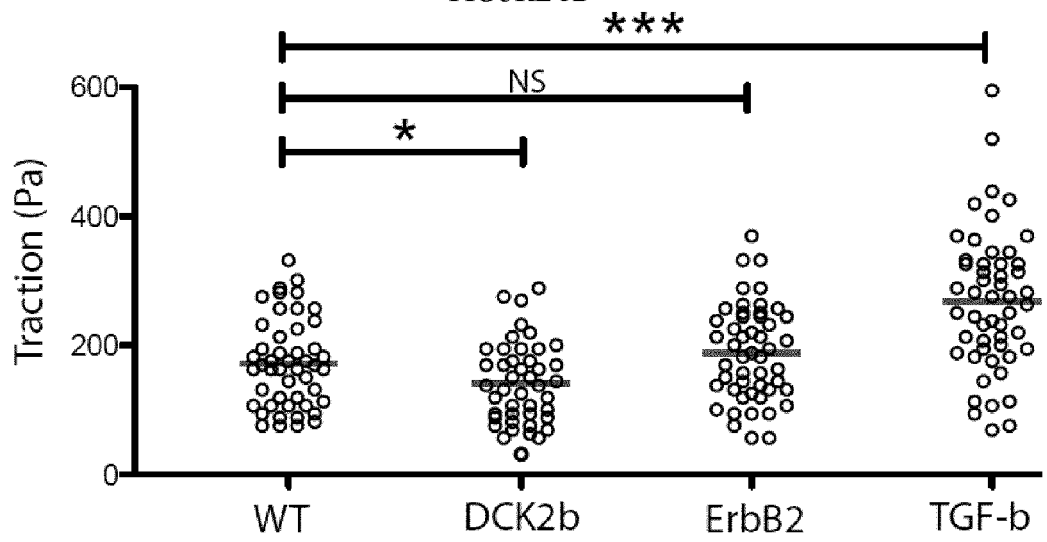

FIG. 5C: Cell traction forces calculated with method illustrated in FIG. 4F in mutant or drug treated MCF10A cells mimicking tumor transformation. MCF10A WT cells were compared to CK2b knockdown cells, ErbB2 inducible cells and TGFb1 treated cells. Comparison between two sets of measures were performed using a Student T test: two tailed, 95% interval confidence: *=$P<0.05$ =$P<0.01$ *=$P<0.001$.

DETAILED DESCRIPTION OF THE INVENTION

The present invention relates to a device suitable for measuring the cellular traction force, to a kit including it, to a method from measuring the cellular traction force using such a device, and to methods for screening or studying molecules. One advantage of the invention is that one local measurement allows the assessment of the global state of contraction of the cell.

Device for Measuring the Cellular Traction Force

The present invention relates to a device suitable for measuring the cellular traction force of one or several cells, said device comprising a soft substrate and disposed thereon an adhesive micropattern having a form suitable to concentrate the cellular traction force on one single point.

Preferably, the substrate presents several adhesive micropatterns disposed thereon. More particularly, said device comprise at least 2 adhesive micropatterns, preferably at least 5, 10, 100, 1 000, 10 000, or 100 000 adhesive micropatterns. In a preferred embodiment, said device comprises between 10 and 50 000 adhesive micropatterns/cm$^2$, more preferably between 5 000 and 15 000 adhesive micropatterns/cm², still more preferably about 10 000 adhesive micropatterns/cm². Preferably, the adhesive patterns are separated by at least 10 µm, preferably by at least 20, 30, or 50 µm.

By "about" is intended the value more or less than 5%.

Soft Substrate

By "soft substrate" is intended a substrate which is deformable (flexible pliable or malleable) when exposed to an external force, in particular to a cellular traction force. Generally, soft substrates are defined by a Young's modulus in pascal (Pa). The soft substrates are adapted to the range of the cellular traction forces to be determined. Therefore, the soft substrates have a Young's modulus of about 0.1 to about 100 kPa, preferably about 0.5 to about 50 kPa, more preferably about 1 to about 20 kPa, and still more preferably about 1 to about 10 kPa. It is intended that the one skilled in the art will adapt this value to the contractibility of the studied cells. For instance, for a cell with a high contraction capacity, less flexible soft substrate will be used. At the opposite, if the cell has a weak contraction capacity, the soft substrate will be very flexible.

In one embodiment, the soft substrate is made of a single material. In another embodiment, the soft substrate is made of a mixture of several materials.

The substrate can be made of any polymer which is not appropriate for cell adhesion or which is treated to become cytophobic (for instance, by coating with a derivative of oligo or poly(ethylene glycol)). Preferably, the substrate is made of any polymer which is not appropriate for cell adhesion.

Non-limiting examples of soft substrates include polyacrylamide gels, poly(N-isopropylacrylamide), poly(2-hydroxyethyl methacrylate) (pHEMA), collagen, fibrin, gelatin, alginate, PDMS (Polydimethylsiloxane) and PVA (polyvinyl acetate). The polymer of the soft substrate may be any hydrogel-forming polymer. For instance, the polymer may be polyethylene glycol or polyacrylamide (PAA). The polymerization may be performed by any means known by one of ordinary skill in the art.

In a particularly preferred embodiment, the substrate is a polyacrylamide gel. The polymerization may be performed from a mixture of acrylamide and a reticulating agent, such as N,N-methylenebisacrylamide. Alternatively, the polymerization may also be performed by radical polymerization. More particularly, the polymerization of polyacrylamide may be performed by radical polymerization in presence of tetramethylethylenediamine (TMEDA) and ammonium persulfate.

The advantage of acrylamide is that it may be polymerized into a gel with a finely-tuned stiffness. Indeed, by varying the relative amounts of monomeric acrylamide and bis acrylamide, the stiffness of the resulting polyacrylamide gel may be increased (by using a higher relative amount of bis acrylamide) or decreased (by using a lower relative amount of acrylamide). Furthermore, the addition of additives such as polypyrrole and poly-ethyl-glycol will alter the stiffness of a polyacrylamide gel. For instance, a preferred weight ratio of monomeric acrylamide and bis acrylamide is in the range between 10:1 to 100:1, preferably between 20:1 to 60:1, more preferably between 30:1 to 50:1, in particular about 40:1.

Otherwise, the soft substrate can be any acrylic acid-based hydrogel constructed by free radical polymerization, such as polyacrylamide, poly(N-isopropylacrylamide), and poly(2-hydroxyethyl methacrylate). The monomeric acrylamide may be cross-linked by any diacrylate group, such as ethylegeglycol dimethacrylate and 1,4-butanediol dimethacrylate, or by N,N' methylenebisacrylamide. The stiffness of the polymerized acrylamide may be tuned by varying the ratio of the cross-linker to the acrylamide subunit. In addition, the stiffness of the gel may be modified by co-polymerizing the acrylamide with other polymers, such as polypyrrole and polyethylene-glycol. The acrylamide may be co-polymerized with polyacetylene group such as polypyrrole and polyaniline to give rise to a conductive polymer.

The soft substrates may also be other soft biocompatible gels such as hydrogels composed of proteins such as gelatin, collagen, arginine, fibrin, and fibronectin, and glycoprotein such as hyaluronate.

Typically, the soft substrate is flat. However, a curved substrate may also be contemplated by the invention.

Optionally, the soft substrate may further include labeled micro-beads homogeneously dispersed in it, preferably fluorescently labeled micro-beads. For instance, carboxylate modified polystyrene fluorescent beads may be used. The convenient micro-beads are well-known in the art (see for instance, Dembo and Wang, 1999, *Biophys J* 76, 2307-2316; Marganski et al., 2003, *Methods Enzymol* 361, 197-211).

The soft substrate is placed on a plate. Preferably, the plate may be formed of a rigid or semi-rigid material, such as plastic, metal, ceramic, glass or combinations thereof. Preferably, the material is convenient for confocal, optical and/or fluorescence microscopies. In the more preferred embodiment, the plate is glass, preferably silanised glass. For example, a convenient plate according to the present invention is a coverslip or a slide.

The device may comprise several groups of adhesive micropatterns on the same substrate or plate separated from each other such that each group can be incubated in a different medium. For instance, a group of adhesive micropatterns can be contacted with a test compound and another group can be contacted with another test compound or without any test compound. This separation can be provided by a physical barrier such as Teflon seal. For example, see SPI Teflon® of SPI Supplies, Teflon® Printed Slides of Aname.

Adhesive Micropatterns

To normalize force production in cells, so that force magnitude can be quantified with a simple measurement of the position of a single region or point, micropattern geometry should concentrate most force application sites on that single region or point. By "a single region" or "a single point" is intended a small area, preferably of less than 100 µm², more preferably of less 25 µm² and still more preferably of about 1-10 µm². By "concentrate" is intended to refer to the fact that a single region or point presents the highest force application. For instance, this single region or point presents a force of at least 300 Pa.

The adhesive micropatterns are such that they present a form suitable to concentrate the cellular traction force on one single region or point. The inventors established the rules for obtaining such micropatterns.

The adhesive micropattern includes an adhesive area comprising an adhesive spreading area and two sets of two adhesive spots, wherein:

a) the adhesive spots are on or close to the convex envelope of the adhesive micropattern;

b) each set contains a spot on either side of an axis in the plane of the convex envelope;

c) the two spots located on same side of the axis are separated by a non-adhesive region forming between 15% and 35% of the total length of the convex envelope;

d) the first set of adhesive spots are essentially located close to or on the axis in order to form an adhesive region of no more than 10% of the total length of the convex envelope; and e) the adhesive spreading area is disposed on each side of the axis between the second set of adhesive spots to connect the two spots and toward the first set of adhesive spots between the two non-adhesive regions of c).

By "convex envelope" is intended the minimal convex polygon containing the adhesive pattern. More particularly, the convex envelope of said micropattern corresponds to the area covered by a cell spread on this adhesive micropattern.

Figure 1A:
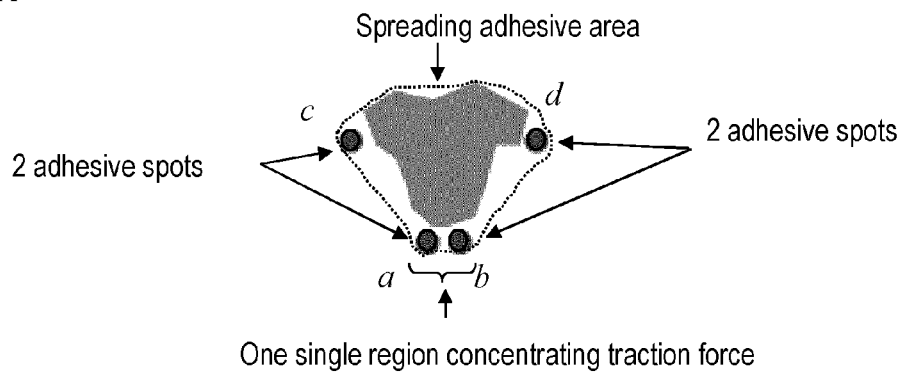
FIG. 1A: This diagram highlights the critical parameters governing the stimulation and orientation of cellular traction forces so that the global level of cell contractibility can be evaluated by the measurement of a single cell point. The micropattern includes an adhesive area, connate or not, to support cell spreading and orient it toward the adhesive spots (Spreading adhesive area). On each of two opposite sides of this adhesive area, the micropattern further includes two adhesive spots separated by a non-adhesive region in order to stimulate the formation and contraction of stress fibers. Traction forces are applied on these spots. One of the two adhesive spots is located at the bottom of the spreading adhesive area. The two bottom adhesive spots (for each side) are closed from each other, leading to a geometrical proximity between the two force application sites, thereby inducing the concentration of the force production on one single region or point. The two bottom adhesive spots (for each side) may be merged into one single spot. Of course, the spreading adhesive area and the four adhesive spots; or the spreading adhesive area and the two of adhesive spots may be merged or fused into on connate adhesive micropattern as illustrated in FIG. 1B. The dashed line illustrates the outline of the cells spread on the micropattern.
Figure 1B:
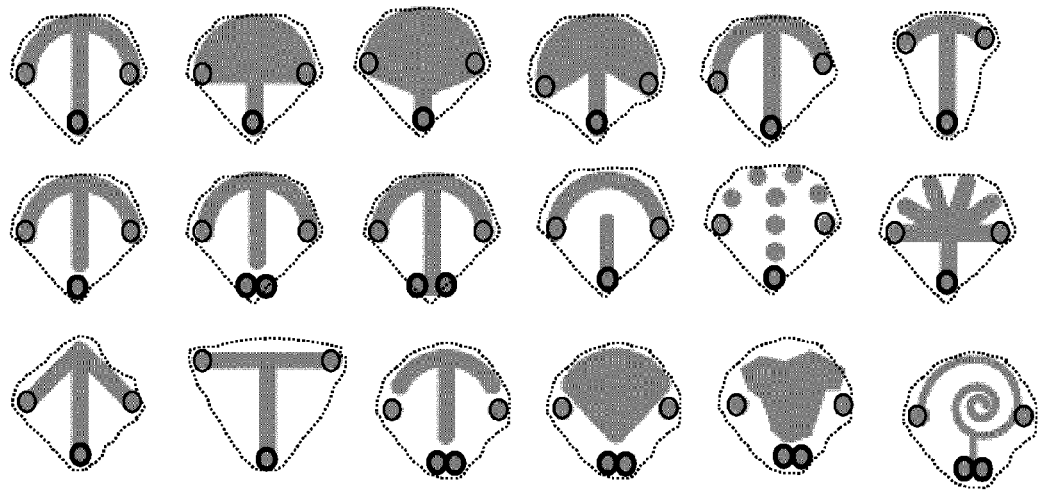
FIG. 1B: Examples of micropattern geometries which can be used to stimulate and focus cellular traction forces on one single region or point. The dashed line illustrates the outline of the cells spread on the micropattern.
Figure 1C:
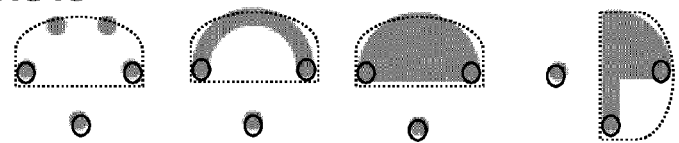
FIG. 1C-G: Examples of micropattern geometries which do not have the property to orient and focus cellular traction forces on one single region or point. The dashed line illustrates the outline of the cells spread on the micropattern.
Figure 1D:
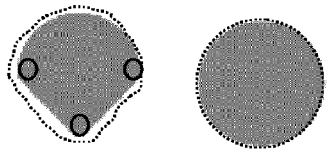
Figure 1E:
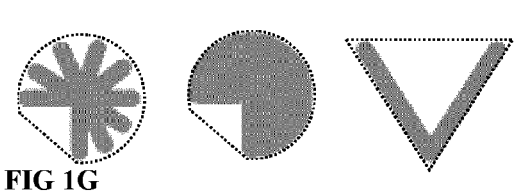
Figure 1F:
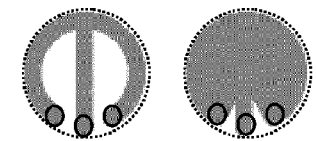
Figure 1G:
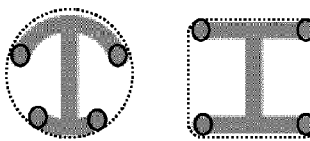
Figure 1H:
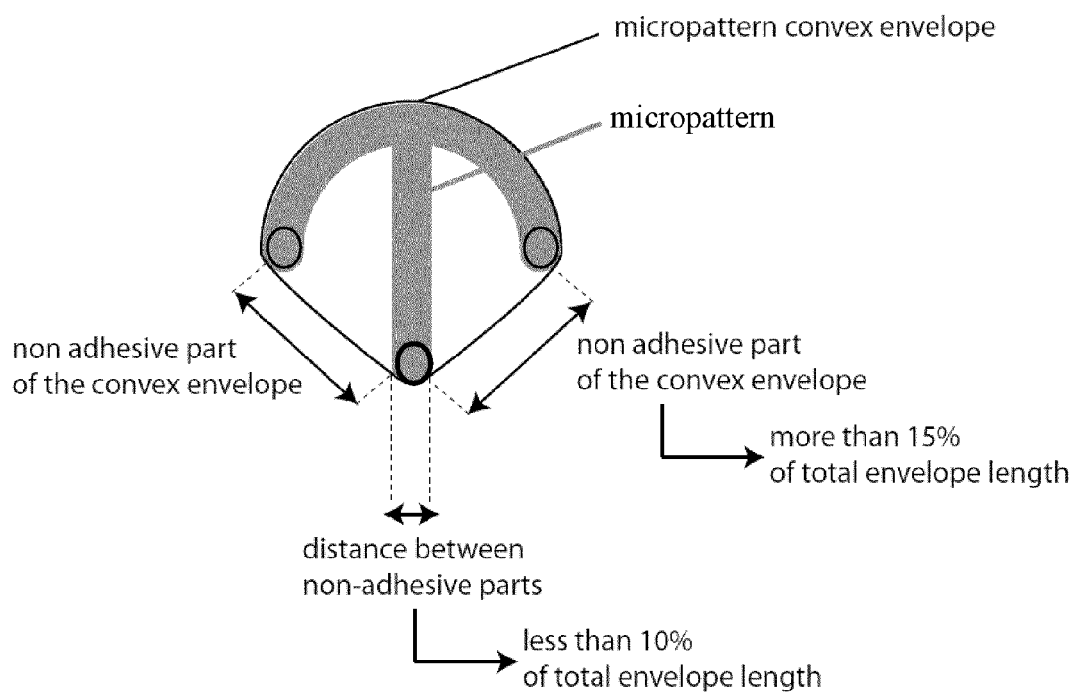
FIG. 1H discloses the features for an illustrative simplistic adhesive micropattern. The adhesive micropattern presents a convex envelope having two non-adhesive parts of each at least 15% of the total envelope length separated by an adhesive part of no more than 10% of the total envelope length.

Indeed, as illustrated in FIGS. 1A and 1H, the adhesive micropattern can be described as comprising a spreading adhesive area and four adhesive spots. By "adhesive spot" is intended to refer a small area, preferably of less than 100 $\mu m^2$, more preferably of less 25 $\mu m^2$ and still more preferably of about 1-10 $\mu m^2$. In respect to an axis (e.g., an axis dividing the inscribed surface of the convex envelope into two equal parts), the micropattern includes two sets of two adhesive spots, each located on either side of the axis (e.g., spots a and b in the first set and spots c and d in the second set, with spots a and c on one side of the axis, and spots b and d on the other side), the surface between two spots located on the same side of the axis being non-adhesive and one set of adhesive spots (e.g., spots a and b) being essentially located close to or on the axis and forming the single region or point concentrating the cellular traction force. The spreading adhesive area is such that it supports cell spreading and orients it toward the four adhesive spots and allow the adhesion of the cell thereon. Optionally, the adhesive spreading area disposed on each side of the axis between the second set of adhesive spots can also be located at the opposite of the first set of adhesive spots (e.g., upper the line joining the spots of the second set c and d of FIG. 1A; see FIG. 1B). Optionally, the axis is a symmetry axis for the adhesive micropattern. The adhesive spots can be optionally merged with the spreading adhesive area. The spots located close to or on the axis can optionally be merged.

The micropattern includes an adhesive area, connate or not, to support cell spreading on a form suitable to concentrate the cellular traction force on one single region or point. In particular, the adhesive spreading area may be connate or not. In the addition, the adhesive spreading area and one, several or all the adhesive spots may be merged.

This form may be defined further by one or several of the following parameters, namely 1) the distribution of adhesive area in respect to the convex envelope of the micropattern, 2) the percentage of adhesive area in respect to the surface inscribed by the convex envelope, and 3) the distribution of adhesive area in respect to the surface inscribed by the convex envelope.

1) The adhesive micropattern is such as the convex envelope of said micropattern includes two non-adhesive parts of each at least 15% of the total envelope length separated by an adhesive part of no more than 10% of the total envelope length, the latter adhesive part forming the single region or point on which the traction forces are concentrated. In a preferred embodiment, the convex envelope has two and only two non-adhesive parts of each at least 15%. However, the convex envelope can further comprise other non-adhesive parts, but small ones (e.g., less than 10% of the total envelope length, preferably less than 5%). In a particular embodiment, the convex envelope includes two non-adhesive parts of each at least 20% of the total envelope length separated by an adhesive part of no more than 5% of the total envelope length. For instance, the convex envelope includes two non-adhesive parts of each between 15% to 35%, preferably between 20% to 30%. More particularly, each of the two non-adhesive parts represents about 15, 20, 25, 30 or 35% of the total envelope length, more preferably about 20, 25 or 30%. In a preferred embodiment, the adhesive part of the convex envelope between the two non-adhesive parts thereof is about 2-10% of the total envelope length, preferably about 5%.

2) The inscribed surface by the convex envelope includes at least 10% of non-adhesive area, preferably at least 15, 20, 25% of non-adhesive area. For instance, the inscribed surface comprises between 10 and 60% of non-adhesive area, preferably between 15 and 50%, and more preferably between 25 and 50%. In a particular embodiment, the inscribed surface by the convex envelope includes about 10, 15, 20, 25, 30, 35, 40, 45, 50, 55 or 60% of non-adhesive area, preferably about 20, 25, 30, 35, 40, 45, or 50% of non-adhesive area.

3) The distribution of adhesive area in respect to the surface inscribed by the convex envelope can be defined by two connate surfaces of the micropattern: the first one is inscribed by the two non-adhesive parts of the convex envelope and the adhesive part separating the two non-adhesive parts (lower surface in respect to the line joining the spots of the second set c and d of FIG. 1A), and the second one is inscribed by the rest of the convex envelope (upper surface in respect to the line joining the spots of the second set c and d of FIG. 1A). The first surface includes less than 50% of adhesive area, preferably less than 45, 40, 35 or 30%. For instance, 5-50% of the first surface may be an adhesive area, preferably 10-30%. This first surface has to include an adhesive area allowing the cell during the spreading to reach and adhere the adhesive part of the convex envelope separating the two non-adhesive parts. However, this surface is preferably essentially non adhesive in order to create a disequilibrium allowing to concentrate the cellular traction force on the adhesive part of the convex envelope separating the two non-adhesive parts. The second surface includes more than 50% of adhesive area, preferably more than 55, 60, 65, 70 or 75%. For instance, the adhesive area of second surface represents 50-100% of the second surface, preferably 60-100%.

The rules deduced from the figures are illustrated in FIG. 1H.

In a preferred embodiment, the micropattern may present a symmetry axis, this axis including the single point or region concentrating the cellular traction force (i.e., the adhesive part of the convex envelope separating the two non-adhesive parts). More preferably, the micropattern may present a single symmetry axis.

Preferably, the axis in the plane of the convex envelope is a median axis of the convex envelope. More preferably, this axis is a symmetry axis. The adhesive micropattern may also be described as including, as illustrated in FIG. 1A:

1) an adhesive spreading area;
2) at each of two opposite sides of this spreading area, two adhesive spots separated by a non-adhesive region (e.g., a and c, and b and d, respectively), one of the two adhesive spots being at the bottom of the spreading area (e.g., a and b).

The above description of the adhesive micropattern indicates a top and bottom of the spreading area just for convenience. Of course, the definition may be adapted if the micropattern is rotated, for instance by 90 or 180°. The adhesive area 1) supports cell spreading and orients it toward the adhesive spots. It may be connate or not. It can be merged with some or all the adhesive spots of 2).

Whatever the way to describe the adhesive micropatterns, it is believed, without being bound by the theory, that the two non-adhesive parts of the convex envelope stimulates the formation and contraction of stress fibers. Traction forces are applied on the adhesive spots or regions bordering the two non-adhesive parts of the convex envelope. The concentration of the force production on one single region or point (namely the adhesive part of the convex envelope between the two non-adhesive parts thereof) results from the geometrical proximity between the two force application sites.

Illustrative examples of suitable micropatterns are shown in FIG. 1B. At the opposite, FIG. 1C-G illustrate non-suitable micropatterns and explain why such micropatterns are not suitable for this use.

The adhesive micropattern can alternatively or in addition be described as comprising an adhesive elongated area, connate or not, and another adhesive element at one of the ends of the elongated adhesive element, in particular roughly perpendicular to the elongated adhesive area. By elongated area is intended a form having a shape factor superior to 3, the shape factor being the ratio between the length of the area and its width. This other element cannot be present at both ends of the elongated element. The elongated area is important for the direct and fast readout of the cellular traction force because it allows placing the highest traction force at the ends of the elongated area and to orientate it. Then, the force measurement step is limited to the measurement of either the displacement of the end and the length of the elongated area.

In a preferred embodiment, the adhesive micropattern presents only one symmetry axis. Preferably, the elongated area or element is the symmetry axis of the adhesive micropattern.

In a particular embodiment, the adhesive micropattern is one of the micropatterns defined in FIG. 1B. In a preferred embodiment, the adhesive micropattern has a shape of crossbow.

The adhesive micropatterns comprise or are made of molecules that promote cell attachment. These molecules are well known to those of ordinary skilled in the art and comprise antigens, antibodies, cell adhesion molecules such as cadherin or fragment thereof, extracellular matrix molecules such as laminin, fibronectin, vitronectin, collagen, synthetic peptides, carbohydrates and the like. Preferably, said adhesive patterns comprise extracellular matrix molecules, more preferably fibronectin.

Preferably, for facilitating the measurement of the position of the single point or area, or of the length of the elongated area, the micropatterns are labeled, preferably fluorescently labeled. However, other labeling such as radioactivity or luminescence may also be contemplated herein. In a preferred embodiment, the molecules promoting cell attachment are labeled, preferably fluorescently labeled. In a very particular embodiment, the molecules promoting cell attachment are fluorescent fibronectin. Alternatively, the molecules promoting cell attachment may be mixed or used in combination with other labeled molecules, preferably fluorescent molecules. For instance, the molecules promoting cell attachment can be mixed with fibrinogen conjugated with a fluorescent dye. In a very particular embodiment, the molecules promoting cell attachment are fibronectin and they are used in combination with fluorescent fibrinogen.

It could also be contemplated that the micropattern is only labeled (preferably fluorescently labeled) on its single point or area, or on its elongated area.

The adhesive pattern of the invention can be suitable for the binding of several cells. Cells will adhere on the adhesive pattern or organize each other so as to orient and concentrate the traction force on the single region or point. Then the determined traction force corresponds to the global force of the group of cells.

In a preferred embodiment, the size of the adhesive pattern is such that only one individual animal or human cell can adhere on said pattern.

Preferably, the convex envelope area of the adhesive micropattern is between 100 to 4000 µm$^2$, more preferably between 200 to 2000 µm$^2$, still more preferably between 500 to 1500 µm$^2$. The area will depend on the number of cells to be adhered thereon and the size of the considered cells. Indeed, the area of the convex envelope generally corresponds to the area of cell spread on the adhesive micropattern.

Preparation of the Device

The device as disclosed herein may be prepared by any technology known in the art. For instance, the device may be prepared as disclosed in WO 2010/011407, the disclosure of which is incorporated herein by reference.

However, the device is preferably prepared by the above detailed method which gives a higher quality of micropattern. Indeed, the inventors designed a new process for the preparation of soft substrates for cell traction measurements involving a key step of in situ gel polymerization and deep-UV activation. The new process allows the preparation of higher homogenous soft substrates having adhesive micropatterns of higher spatial resolution. The process is illustrated in FIG. 2A.

The devices of the present invention may be prepared by a process comprising the steps of:
(a) producing a polymer between a plate and a non-transparent mask comprising at least one transparent area having the form of the adhesive micropattern as defined above,
(b) exposing the polymer to deep UV through the mask,
(c) detaching the mask from the polymer,
(d) contacting the polymer with a molecule that promotes cell attachment, and
(e) optionally washing away the excess of molecule.

Step (a) comprises the production of a polymer between a plate and a mask. The plate may be as defined above in the device section.

The produced polymer may be any synthetic biocompatible polymer, in particular gel-forming polymer. The polymerization may be performed by any means known by one of ordinary skill in the art by implementing polymerization reagents. For instance, the produced polymer according to step (a) may be a polyethylene glycol or polyacrylamide (PAA). It can also be a co-polymer formed with acrylamide and any other polymer, such as polyethylene glycol or polypyrrole. The polymerization reagents are preferably added as a solution onto the mask and then the plate is applied thereon, as to form a "sandwich" between the plate and the mask. Polymerization then occurs and the formed polymer may present finely-tuned stiffness. The polymer can be more particularly any acrylic acid-based hydrogel constructed by free radical polymerization, such as polyacrylamide, poly(N-isopropylacrylamide), or poly(2-hydroxyethyl methacrylate). The monomeric acrylamide may be cross-linked by any diacrylate group, such as ethyleneglycol dimethacrylate and 1,4-butanediol dimethacrylate, or preferably by N,N' methylenebisacrylamide. The stiffness of the polymerized acrylamide may be tuned by varying the ratio of the crosslinker to the acrylamide subunit. By way of example, when a polyacrylamide is prepared, by varying the relative amounts of monomeric acrylamide and bis acrylamide, the stiffness of the resulting polyacrylamide gel may be increased (by using a higher relative amount of bis acrylamide) or decreased (by using a lower relative amount of acrylamide). In addition, the stiffness of the produced gel may be modified by co-polymerizing the acrylamide with other polymers, such as polypyrrole and polyethylene-glycol. The acrylamide may be co-polymerized with polyacetylene group such as polypyrrole and polyaniline to give rise to a conductive polymer. For instance, a preferred weight ratio of monomeric acrylamide and bis acrylamide is in the range between 10:1 to 100:1, preferably between 20:1 to 60:1, more preferably between 30:1 to 50:1, in particular about 40:1. In an embodiment, the polymer is polyacrylamide and the polymerization is performed by radical polymerization in presence of tetramethylethylenediamine (TEMED) and ammonium persulfate. The thickness of gel could range from 20 to 200 μm, preferably between 50-100 μm.

In an embodiment, fiducial markers such as labeled beads, preferably fluorescently labeled beads, can be added during step (a). The markers are generally mixed with at least one of the polymerization reagents prior to polymerization. For instance, carboxylate modified polystyrene fluorescent beads may be used. The convenient micro-beads are well-known in the art (see for instance, Dembo and Wang, 1999, *Biophys J* 76, 2307-2316; Marganski et al., 2003, *Methods Enzymol* 361, 197-211). However, once the calibration curve is determined for one type of adhesive micropattern and soft substrate, there is no need labeled beads into the substrate. Accordingly, this embodiment is contemplated in order to prepare the calibration curve.

As mentioned before, polymer may be produced on the non-transparent area mask comprising at least one transparent area having the form of the adhesive micropattern. Transparent areas correspond to surfaces of the mask that are transparent to the deep UV light used in step (b). Transparent areas are made of any material that is transparent to the deep UV light used in step (b). For instance, the transparent areas of the mask may be made of quartz. The non-transparent mask (also simply named the mask in the present description) may also be defined by the possibility of coexistence of two types of areas: transparent and non-transparent areas. Non-transparent areas are made of any material that is opaque to the deep UV light used in step (b). For instance, the non-transparent areas of the mask may be made of chromium. According to this embodiment, the chromium layer defines the non-transparent areas. The mask may be a quartz plate coated with a chromium layer, where the chromium layer is absent on specific areas, defining thereby the transparent areas. In this particular embodiment, mask is a quartz plate partially coated with a chromium layer. In this particular embodiment, the mask comprises non transparent areas where the quartz plate is coated with a chromium layer and transparent areas where the quartz plate is uncoated with a chromium layer. The transparent areas define areas potentially activated by UV and therefore where adhesive patterns are desired. Preferably, the mask presents several transparent areas, defining adhesive micropatterns disposed on the gel. More particularly, said mask comprises at least 2 transparent areas, preferably at least 5, 10, 100, 1 000, 10 000, or 100 000 transparent areas. In a preferred embodiment, said mask comprises between 10 and 50 000 transparent areas/$cm^2$, more preferably between 5 000 and 15 000 transparent areas/$cm^2$, still more preferably about 10 000 transparent areas/$cm^2$. Preferably, the transparent areas are separated by at least about 10 μm, preferably by at least about 20, 30, or 50 μm.

Step (b) corresponds to the irradiation of the formed polymer through the mask with deep UV (ultraviolet). In the present invention, deep UV refers to UV radiation with a wavelength inferior to 200 nm, in particular inferior to 190 nm and more specifically equal to 180 nm. Step (b) may be for instance performed in a UV/ozone cleaner. UV irradiation triggers activation of the polymer gel in the areas of the polymer exposed to the UV irradiation through the transparent areas of the mask. Further to irradiation, in said areas, the polymer may become activated for at least one molecule that promotes cell attachment. The polymer may alternatively become activated for functionalization with a coupling agent (or linker) that will make the functionalized polymer activated for at least one molecule that promotes cell attachment. One advantage of the use of deep UV radiation is that no photoinitiator is necessary to create free radicals.

In step (c), detachment of the mask may be performed by any means known by one of ordinary skill in the art. Removal of the mask may be simply performed by manual removal.

In step (d), contacting the polymer to the solution comprising a molecule that promotes cell attachment may be performed by any means known by one of ordinary skill in the art. The molecule can be as defined above. Step (d) may be preferably divided into two steps: (d1): contacting the polymer with a coupling agent (or a linker), optionally in presence of a catalyst, and, (d2): contacting the functionalized polymer obtained after step (d1) with the molecule. The coupling agent may be a heterobifunctional crosslinker like EDC (1-ethyl-3-(3-dimethylaminopropyl) carbodiimide), or SMCC (Succinimidyl 4-[N-maleimidomethyl]cyclohexane-1-carboxylate); or a homobifunctional crosslinker like DSG (Disuccinimidyl glutarate). According to a preferred embodiment, the coupling agent is EDC. The catalyst may be for instance NHS (N-hydroxysuccinimide). In the present invention, a "linker" or "coupling agent" refers to a molecule that may be associated with the polymer to link the polymer to the molecule that promotes cell attachment.

In step (e), the excess of molecule that promotes cell attachment and optionally other chemical components of step (d) may be washed away, for instance with water or any other appropriate solvent, including alcoholic solvent, such as isopropanol. The process may additionally comprise a step comprising detaching the polymer from the plate. This step may be performed in particular after step (e).

Contrary to the processes implemented in the art to produce currently used soft substrates, this process does not include any intermediate between the mask and the gel. Classically, the fabrication processes imply the use of a mask to create a mold such as a stencil or a stamp, and then the application of the mold onto the polymer gel. The absence of intermediate and the in situ polymerization trigger a high spatial resolution. Thus, the contours of the micropatterns on the gel, corresponding to the transparent areas of the mask that have been affected by the UV irradiation, are precisely defined. Further, as the process comprises less microfabrication steps than the previously described processes, it is faster and easier to implement.

Method for Measuring the Cellular Traction Force

The device as detailed above may be used for assessing the cell contraction, in particular for measuring a cellular traction force of a cell.

The present invention relates to a method for measuring a cellular traction force of one or several cells, comprising:
  providing a soft substrate having disposed thereon an adhesive micropattern having a form suitable to concentrate the cellular traction force on one single region or point;
  exposing the substrate to at least one cell for a period of time sufficient to allow the cell(s) to bind to the adhesive micropattern;
  measuring the position of said single region or point of said micropattern; and
  calculating the displacement of said single region or point of said micropattern, thereby determining the cell traction force.

The use of a micropattern areas defined herein allows the determination of the cellular traction force just by the measurement of the position change of the single region or point on which is concentrated the cell contraction. Consequently, cell traction forces could be rapidly and accurately quantified by a single micropattern picture acquisition and position measurement.

Indeed, a calibration curve may be established and it provides a relationship between the position change of the single region or point of the adhesive area and the cellular traction force. In a preferred embodiment, the relationship is linear. This calibration curve depends on the soft substrate and the adhesive pattern.

For preparing the calibration curve, the traction force is measured by usual methods well-known by the one skilled in the art, in particular by Traction Force Microscopy (TFM) (e.g., Dembo and Wang, 1999, *Biophys J* 76, 2307-2316). In order to prepare this calibration curve for a device with a defined soft substrate and defined micropatterns, a soft substrate with labeled micro-beads homogeneously dispersed in it, preferably fluorescently labeled micro-beads, is prepared and used for TFM. Briefly, when cells attached to the soft substrate, due to the traction force exerted by the cell, the soft substrate deformed and thus the beads displaced. By comparing the image of the displaced beads and another image of the original beads position taken after detaching the cell (e.g., by trypsin treatment or optionally before the cell attachment), one can obtain the displacement field. The traction force could therefore be obtained by solving a displacement-force inverse problem. In particular, the Example section provides details for preparing the calibration curve.

It is important to note that a calibration curve prepared for a defined soft substrate and defined micropatterns can be used for each device having the defined soft substrate and defined micropatterns. It is not necessary to prepare a calibration curve for each device. This is why the present invention also relates to a kit comprising a device as detailed above with a defined soft substrate and defined micropatterns and a corresponding calibration curve. Therefore, the labeled micro-beads are no more necessary once a calibration curve has been established for a specific device.

Therefore, the cellular traction force is determined from a calibration curve showing the relationship between the cellular traction force and the position change of the single region or point of said micropattern.

Alternatively, the position change can also assessed by measurement of the length of the elongated area when the adhesive micropattern is described as comprising an adhesive elongated area, connate or not, and another adhesive element at one of the ends of the elongated adhesive element.

Cells will adhere on the adhesive pattern or organize each others so as to orient and concentrate the traction force on the single region or point. Then the determined traction force corresponds to the global force of the group of cells.

However, in a preferred embodiment, the method is for measuring a cellular traction force of one cell and the micropattern is such that only one individual animal or human cell can adhere on said micropattern.

The device used in the method is as defined in the above section.

Preferably, the cell to be studied is seeded onto the micropattern by exposing the substrate to it for a period of time sufficient to allow the cell(s) to bind to the adhesive micropattern. Then, they are cultured in the suitable conditions for the defined cells.

Preferably, the micropatterns are labeled, preferably fluorescently labeled. The determination of the position of the single region or point, or the elongated area length is performed by a micropattern picture acquisition through microscopy.

Any kind of cells can be used in the present invention. Preferably, the cells are eukaryotic. Cells can be from animal, mammalian, or human. Cells can be for example fibroblasts, mesanchimal cells, endothelial and epithelial cells. Cells can also be muscle cells or nerve cells. Muscle cells include smooth muscle cells, striated muscle cells, or cardiac cells. Cells can also be stem cells such as embryonic stem cells (primary and cell lines), fetal cells (primary and cell lines), adult stem cells and induced pluripotent stem cells (iPS). Cells can be derived from a healthy or pathologic tissue or organism. Accordingly, cells can be normal or abnormal cells. The cells can be wild type or modified cells (physically or genetically altered cells). In a particular example, the cells can be tumor cells. For example, a gene can be inactivated and these methods allow the identification of genes which are involved in the cellular traction force.

In a first embodiment, a single type of cells is seeded onto the micropatterns of the substrate. Alternatively, several types of cells may be seeded onto the micropatterns of the substrate so as to determine the cellular traction force for each type of cells. For instance, normal and abnormal cells may be compared; or wild type and modified cells, and the like.

Accordingly, the present invention relates to a method for determining the difference of cellular traction of two types of cells, comprising:
  measuring the traction force of a first type of cells by the method as defined above;
  measuring the traction force of a second type of cells by the method as defined above; and,
  comparing the traction force of the first and second types of cells, thereby determining the difference of cellular traction of the two types of cells.

For instance, the method may be useful for investigating a disease pathology, for studying tissue biology, and the like.

In another embodiment, a single type of cells is seeded onto the micropatterns of the substrate but the cells may be contacted to one or several molecules so as to determine the impact of the molecule(s) on the cellular traction force of cells.

Accordingly, the present invention relates to a method for determining the effect of a candidate/test molecule on the traction force of a cell, comprising:
  measuring the traction force of a cell by the method as defined above;
  measuring the traction force of the cell incubating with the candidate/test molecule by the method as defined above; and,
  comparing the traction force of the cell incubating or not with the candidate/test molecule, thereby determining the effect of the candidate/test molecule on the traction force of the cell.

Optionally, the effect of the candidate/test molecule may be compared to a reference molecule having a well-defined effect. The candidate/test molecule may increase the traction force of the cell or decrease it.

The candidate/test molecule may be incubated with a cell by any suitable means. For example, it may be added dropwise on the cell and allowed to diffuse in the cell. It may be added with the culture medium. More complex high throughput system with microfluidics handling system may also be contemplated.

For instance, the method may be useful for drug discovery, for testing toxicity of the candidate/test molecule on cells, for identifying molecules that modulate cellular contraction, for identifying molecules useful for treating or preventing a disease, and the like. In particular, the disease may be a cancer.

In an additional embodiment, several types of cells may be seeded onto the micropatterns of the substrate and contacted to one or several molecules so as to determine the impact of the molecule(s) on the cellular traction force of each type of cells.

In these embodiments, a device comprising several groups of adhesive micropatterns on the same substrate or plate separated from each other such that each group can be useful.

The candidate/test molecule may be of various origin, nature and composition. It may be any organic or inorganic substance, such as a lipid, peptide, polypeptide, nucleic acid, sugar, small molecule, chemical agents, drugs, etc., in isolated or in mixture with other substances. For instance, the test compound can be an antibody, an antisense oligonucleotide, or an RNAi. The molecule may be all or part of a combinatorial library of products, for instance.

This invention is further illustrated by the following examples which should not be construed as limiting. The content of all references cited throughout the specification is incorporated herein by reference.

EXAMPLES

Example 1

Cell ability to exert traction forces on their microenvironment through the development of intra-cellular tension strongly impacts cell physiology and notably tumoral transformation. Current methods to measure cell traction forces rely on the deformation of soft substrates. Exact forces cannot be directly inferred from deformation since local deformation result from both local and distant force application sites. Accurate measurements require either long calculations or sophisticated microfabrication steps to numerically or physically separate force application sites.

The inventors developed a new method to associate the control of the spatial distribution of cell traction forces on adhesive micropatterns with force measurement on soft deformable substrates. Cells pull on the micropattern and, on appropriate geometries, contract micropattern length in a standardized fashion. After a calibration of the force-deformation relationship, cell traction forces could be rapidly and accurately quantified by a single micropattern picture acquisition and length measurement.

The inventors applied this method to mammary epithelial cells traction force measurements in various conditions mimicking specific tumoral transformations. They found that, contrary to the current view, all transformation phenotypes were not associated to increased level of cell contractility.

Results

New Micropatterning Method on Soft Substrate

The inventors used direct exposure of PAA to deep UV through an optical mask to rapidly achieve micropatterning with high spatial resolution and reproducibility in order to precisely orient cell actin cytoskeleton in large-scale experiments (see Materials and Methods). A drop of acrylamide solution was placed directly on the chromium optical mask and covered with a silanized glass coverslip. After PAA polymerization, the sandwich was exposed to deep UV in order to oxidize the PAA through the micropatterned transparent regions of the optical mask (FIG. 2A). The coverslip along with the PAA gel was removed from the mask and coated with fibronectin, which adsorbed only on the UV-exposed regions. The direct contact with the optical mask during PAA polymerization and UV-exposure allowed a faithful reproduction of its spatial features and ensured a good, sub-cellular, spatial resolution (FIG. 2B). The coating was quite homogeneous over the entire coverslip (FIG. 2C). The entire process, from PAA preparation to the end of protein coating, lasts 2 hours, including 1 hour of PAA polymerization, and is highly robust.

Controlled Localization and Focusing of Force Application Sites

Figure 3A:
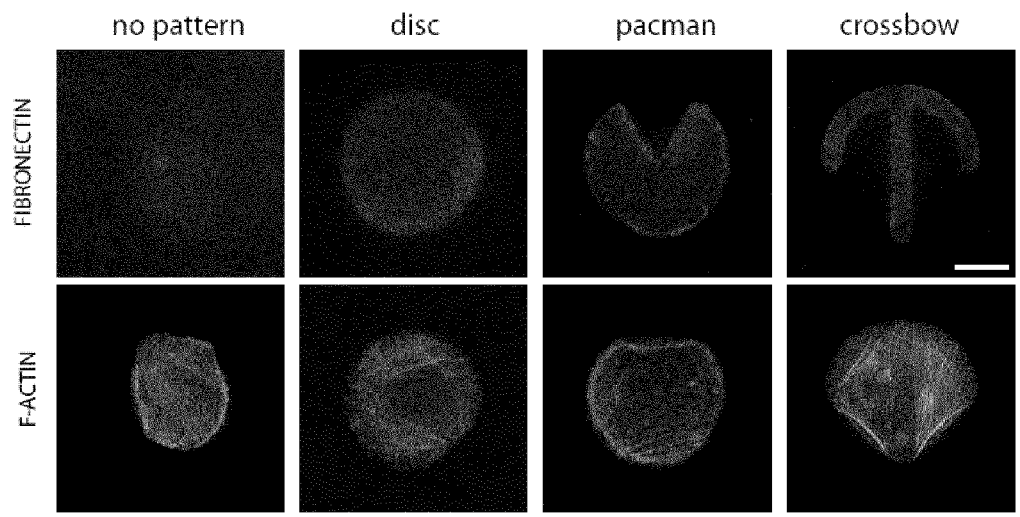
FIG. 3A: Micropattern geometry orients actin network architecture. Individual MCF10A cells plated either on non-patterned, fibronectin coated, glass slide, or on disc, or pacman or crossbow shaped fibronectin micropatterns. Cells were fixed and stained with phalloidin to reveal F-actin filaments. Cells form preferentially contractile F-actin bundles, or stress fibers, above non-adhesive regions.
Figure 3B:
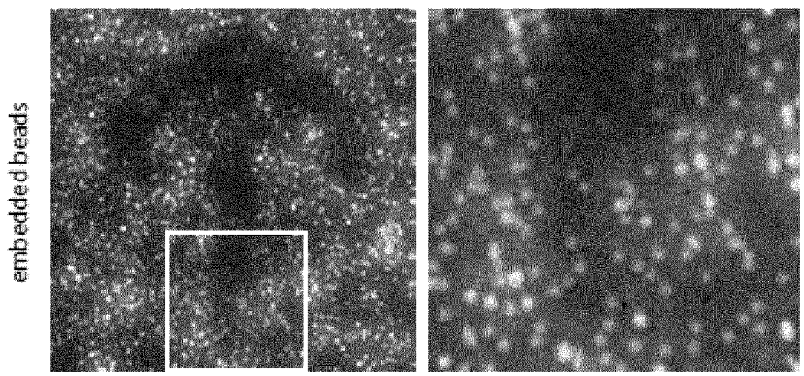
FIG. 3B: Gel embedded beads were used to calculate cell traction force with Fourier transform traction cytometry. Pictures of beads were taken before and after cell detachment with trypsin to visualize gel deformation upon cell traction forces. Bead displacement were automatically detected and processed to infer the corresponding traction force field (see Materials and Methods).
Figure 3C:
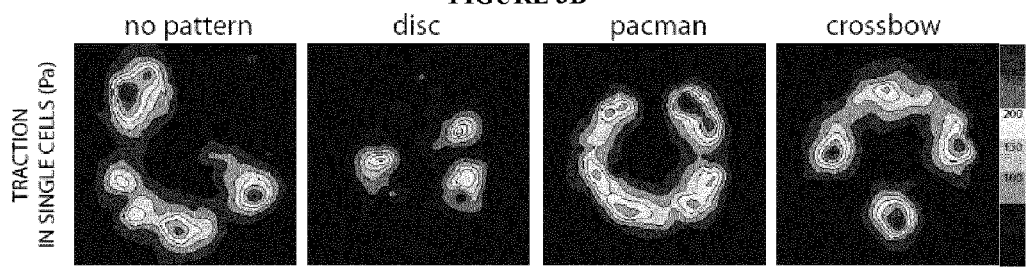
FIG. 3C: Traction force field calculation shows that cell exhibit unpredictable stress spatial distribution in non-patterned and in disc-shaped patterned cells. Cells patterned on pacman, and crossbow, develop enhanced traction forces on adhesion sites flanking non-adhesive regions.
Figure 3D:
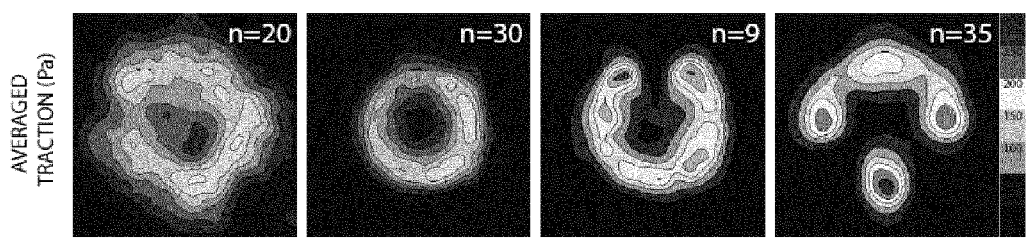
FIG. 3D: Overlaying and averaging of traction force fields highlight the variability of traction force field in non patterned cells. Non patterned cells were aligned using their nucleus position. Force fields were more precisely quantified in micropatterned cells. Crossbow shaped micropatterns reproducibly concentrate the location of cell traction forces in the bottom part of the vertical bar.

Non-tumorigenic human epithelial cells from the mammary gland, MCF10A, were plated on the micropatterned PAA substrates. Cells specifically attached to the fibronectin coated micropatterns since non-exposed PAA regions prevented protein adsorption (FIG. 2D). The effect of micropattern geometry on cell traction forces orientation was tested on various shapes: disc, pacman and crossbow (FIG. 3A). Spread cells exerted traction forces on the micropattern that could be measured by looking at the displacement of fluorescent beads embedded in the PAA gel (see FIG. 3B and Material and Methods). Particle Image Velocimetry followed by individual particle tracking were used to measure bead displacements (Marganski et al (2003) *Methods Enzymol* 361:197-211; Sabass et al (2008) *Biophys J* 94(1):207-220). Force fields were calculated from the bead displacement fields by using the Fourier transform traction cytometry (Sabass et al, supra; Butler et al (2002) *Am J Physiol Cell Physiol* 282(3):C595-605). Force fields exerted by individual cells were overlaid and averaged to quantify their reproducibility (FIG. 3C,D). On homogeneously coated regions cells developed forces that were randomly distributed from one cell to the other. In cells constrained on disc shaped micropatterns, forces were still randomly oriented but their magnitudes were lowered due to reduced cell spreading. In cells constrained on pacman shaped micropatterns, forces distribution was geometrically biased due to enhanced cell contraction above non adhesive regions. Cell ability to exert traction forces was even more stimulated on crossbow shaped micropatterns, where the total traction force per cell was higher than on any other micropattern shape (FIG. 3D). Importantly, most of the traction forces were reproducibly oriented upward, along the straight adhesive bar on the extremity of which the inventors measured the highest pressure (FIG. 3D). These results demonstrated that appropriate micropattern geometries can both stimulate cell contraction and orient force application. Such geometries place cells in convenient conditions to reveal cell potential contractility and measure their contraction strength.

Force Field Streamlining Allows Reproducible Force-Deformation Relationship

When actin cables have an unpredictable spatial distribution, a given deformation cannot be directly assigned to a defined force magnitude. Indeed, forces applied on adjacent adhesion sites both affect local deformations, due to the continuous nature of the substrate. Each deformation results from local and distant forces. So the calculation of the force field is highly dependent on the spatial distribution of force application sites and the relationship between deformation and forces varies from one cell to the other. The inventors hypothesized that in cells developing a reproducible architecture and a controlled pattern of force application, a given local deformation could be assigned to a defined value of the contractile force. To test this hypothesis, they used classical force field calculations with beads embedded in the PAA gel (FIG. 3B) and observation of micropattern deformation (FIG. 4A) to establish the force-deformation relationship in micropatterned cells. On disc, deformation orientation was unpredictable and no good correlation could be found between the deformation along a reference axis and the average traction force all over the cell (FIG. 4B). When the deformation was measured along the shortest, and therefore most contracted, cell axis, the correlation was improved (FIG. 4C). However this shape did not stimulate cell contraction and therefore did not fully reveal cell contractility potential (FIG. 3D). Cell traction force magnitudes were slightly higher on pacman shapes, but force and deformation were not precisely correlated (FIG. 4D). On the crossbow, the length of the straight bar is compressed in response to cell traction forces (FIG. 4A). The inventors found a good linear correlation between crossbow bar shortening, a local measure, and average cell traction, a global cell state (FIG. 4E). Each length variation could be assigned to a defined force value. This showed that crossbow bar length could be taken as a direct indicator of cell contraction level. On the crossbow, a single image acquisition was sufficient to measure the bar length and read the corresponding average cell traction force using the calibration curve (FIG. 4F). It was no longer necessary to measure embedded bead displacements or to perform long numerical calculations to solve the inverse problem and obtain the corresponding force value. Force measurement was not only easier and faster, compared to any previous method, it also became amenable to automation.

Validation of Force Measurement

The inventors validated this methodology by analyzing the well-described Blebbistatin effects on cell contractility. Blebbistatin has been shown to inhibit myosin-II ATPase. Cells were treated with increasing dose of Blebbistatin. Crossbow bar length measures on thresholded pictures of fluorescent micropattern were used to measure cell traction forces (FIG. 5A). The force inhibition profile in response to increasing dose of Blebbistatin matched the myosin II inhibition profile and the cellular force profile measured with other techniques (Mitrossilis D, et al. (2009) *Proc Natl Acad Sci USA* 106(43):18243-18248). Drugs effects on cell contractility could thus easily and rapidly been quantified using this new methodology.

Another application requiring numerous, and thus fast, force measurements is the analysis of force relaxation over time. The inventors could also follow force magnitude decrease in response to 50 µM of Blebbistatin and found that it follows a single exponential decay (FIG. 5B).

All Tumorigenic Transformation do not Increase Cell Contractility

The inventors then used their method to compare the contraction level of wild type (WT) MCF10A cells to that of drug treated or genetically modified MCF10A cells mimicking some tumor transformation. Indeed tumor transformation has been shown to be associated with high levels of cell contraction. This suggested that cell contraction level measurements are required to understand the regulation of tumor progression and to develop improved treatments. Cell exposure to TGFb1 is known to induce epithelial to mesenchymal transition, which mimics some features of tumor transformation. TGFb1 treated cells are unable to form proper acinar structures when cultured on collagen gels. Instead they proliferate and form unstructured cell groups recapitulating tumor growth. MCF10A cells were treated for 2 days with 2 ng/mL of TGFb1 before being plated on micropatterned PAA substrates. As expected, cells exhibited a significantly higher level of cell contraction as revealed by crossbow shortening (FIG. 5C). ErbB2 receptor activation is known to induce early stages of mammary carcinogenesis and prevent proper acinar structure formation in collagen gels. The inventors activated ErbB2 receptors with the ligand AP1510 in MCF10A expressing inducible ErbB2 receptor. Surprisingly, they found no significant changes in the level of cell contraction. Protein kinase CK2 (previously known as Casein Kinase 2) inactivation has also been shown to induce epithelial to mesenchymal transition and participate in tumor transformation and propagation. Interestingly, in CK2b knockdown cells, the contraction level was significantly lower than in WT cells (FIG. 5C). These results show that various types of tumorigenic transformation can either promote or reduce the level of cell contraction. They also demonstrate that the method of the inventors can easily be used at larger scale to characterize more precisely this complex correlation between cell contraction and tumoral transformation.

DISCUSSION

The use of deep UV exposure on PAA in contact with the photomask is to the inventors' knowledge the most robust and easiest method to create homogeneous and reproducible micropatterns on soft deformable substrates. The actin network streamlining and force field normalization in response to appropriate micropattern geometry allow a precise calibration of the relationship between micropattern shape deformation and traction forces. When force application sites are isolated from other sites by non-adhesive regions, the natural linear relationship between force and deformation of soft substrate is recovered, probably because deformation fields from each force application sites do not cross-over. Thanks to this linear relationship between force and deformation, force measurement is simply obtained by measuring micropattern length. Classical force measurement methods are still required to obtain the calibration curve. But, afterwards, a single image acquisition is sufficient to measure micropattern length and read the corresponding traction force. Therefore, force measurement is as simple as with the use of micropillars (Tan J L, et al. (2003) *Proc Natl Acad Sci USA* 100(4):1484-1489) without the microfabrication constraint and issues of cells spreading in between the pillars. In addition, the inventors' method is easily amenable to automation since cell position and subcellular localization of force production are precisely controlled. This method paves the way to large scale and high throughput analysis of cell contraction state.

The initial work of the inventors identified tumorigenic transformations that were not associated to increased level of cell contractility. High levels of contractility were observed in epithelial cells forming disorganized multicellular structures or detaching from each other. Such phenotypes are characteristic of advanced or late stages of tumoral transformation. ErbB2 receptor activation is a feature of early tumoral transformation that impacts on growth rate. CK2 is also implicated in anti-apoptotic effect and CK2beta knockdown specifically affect p53-dependent cell survival. Although contractility activates cell growth, early phases of cancer progression involving cell growth stimulation might not systematically be associated to high level of contractility. It would now be necessary to analyze more specifically cell contraction level at various phases of tumoral transformation to clarify the relationship between cancer progression and cell contraction. Mechanical property characterization of healthy and transformed cells could then be used to set up a new medical diagnosis test.

Materials and Methods

PAA Micropatterning 25 mm round glass coverslips were first cleaned with piranha for 2 hour and silanized by dipping in ethanol solution containing 2% (v/v)3-(Trimethoxysilyl)propyl methacrylate (Sigma) and 1% (v/v)acetic acid for 5 min. After cleaning with ethanol to remove excess silane residue, the coverslips were incubated at 120° C. for one hour.

Carboxylate modified polystyrene fluorescent beads (dark red 200 nm, Invitrogen F-8807) were passivated by poly (ethylene)glycol as follow: fluorescent beads were diluted 25-fold in MES buffer (10 mM pH 5.5) containing 8 mg/mL N-hydroxysuccinimide (NHS; Fluka) and 4 mg/mL EDC (1-Ethyl-3-[3-dimethylaminopropyl]carbodiimide Hydrochloride; Pierce) before 1:1 mixing with PLL-PEG (PLL(20)-g[3.5]-PEG(2); Susos) solution (4 mg/mL in 10 mM pH8.5 HEPES buffer). The mixture was incubated with rotation at 4° C. overnight. The beads were subsequently spun down and resuspended in HEPES buffer (10 mM pH7.4).

Acrylamide solution containing 6.67% acrylamide and 0.167% bis-acrylamide was mixed with passivated fluorescent beads by sonication before addition of APS and TEMED. A drop of acrylamide solution was put directly on the chromium side of the photomask (Toppan). The photomask was cleaned by n-Hexane prior to use in order to maintain a hydrophobic surface. A silanized coverslip was placed over the drop and let it polymerize for 45 minutes. The sandwich was then exposed to deep UV in a UV/Ozone cleaner (Jelight) for 3 minutes. The coverslip with gel was carefully removed from the mask and incubated with 10 mg/mL EDC and 17 mg/mL NHS water solution for 15 minutes, and then coated with 20 ug/mL fibronectin (Sigma) and 5 ug/mL Alexa546 conjugated fibrinogen (Invitrogen) in HEPES buffer (10 mM pH 8.5) for one hour. The photomask was washed with water and then isopropanol.

AFM Measurement of Micropatterned PAA Elasticity

All atomic force microscopy (AFM) measurements were carried out in PBS using a PicoPlus AFM (Agilent Technologies, USA). The spring constant of each cantilever was determined using the thermal noise method (Butt & Jaschke (1995) *Nanotechnology* 6(1):1-7). Force-indentation profiles were recorded using borosilicate sphere-tipped cantilevers with a radius $R=2.5$ μm (Bioforce Nanoscience, IA, USA) and a spring constant of 60 mN/m. To delimitate insolated and non-insolated zones, topographies of $60 \times 60$ μm$^2$ were first imaged in contact mode with $512 \times 512$ pixels$^2$ at line rates of 0.5 Hz and with the same cantilevers. The sphere probe was then moved above the zone of interest before indentation. The Young's moduli E were extracted from the above profiles using the Hertz sphere model for the indentation of a semi-infinite solid. All polyacrylamide samples were assumed to be incompressible (Boudou et al (2006) *Biorheology* 43:721-728). The expression of the indentation force is thus given by:

$$F = \frac{16E}{9} R^{1/2} \delta^{3/2}$$

where d is the indentation. d is obtained by subtracting the deflection d from the movement of the piezoelectric ceramic ($Dz=z-z_0$) in the z direction, where $z_0$ is the contact point, which was determined following the method proposed by Crick and Yin (2007, *Biomechanics and Modeling in Mechanobiology* 6(3):199-210). For each sample probed, two measurements were taken at five positions. A perfect overlap of two successive indentations performed at each position was obtained, which indicates that the samples were only elastically and not plastically deformed. Young's moduli were calculated by least-square fitting of the experimental force-indentation curves. Measured Young modulus of UV exposed regions was 7.29+/−0.42 kPa. Measured Young modulus of non-exposed regions was 6.64+/−0.59 kPa.

Traction Force Measurement

Bead Displacement Analysis

Displacement fields describing the deformation of the PAA substrate are determined from the analysis of fluorescent beads images before and after removal of the adhering cells with trypsin treatment. First, the images are corrected for any translational drift that may have occurred during the experiment by cross-correlating the entire images. The distance of the correlation function maximum from the origin stands for the global translation between the images, which can then be corrected by shifting one image with respect to the other.

The displacement field is obtained in two steps (Sabass et al (2008) *Biophys J* 94(1):207-220; Butler et al (2002) *Am J Physiol Cell Physiol* 282(3):C595-605). Both images are divided into non-overlapping windows (5.76 μm squares). In the first step, coarse deformations are computed by cross-correlating each window in one image to the window at the same location in the other image. The result is used to shift one window with respect to the other, so that the global displacement is compensated and only local displacements remain. The second step of the analysis consists in detecting and tracking the beads in the aligned windows, in order to retrieve beads displacements with maximum spatial resolution. Summing the displacements obtained for each step yields the total displacement at the position of the detected beads. The present two-step method provides more reliable results in the case of large displacements or densely packed particles compared to standard particle tracking. Indeed, since part of the total displacement can be corrected following the correlation-based analysis, the cutoff distance in the tracking procedure can be reduced so that different beads would not get mixed up. In addition, compared to pure correlation analysis, the present technique benefits from the intrinsic spatial accuracy of particle tracking since the information relative to each individual bead can potentially be retrieved.

A special procedure is used to evaluate displacements in the area of the adhesive pattern where gel deformation is expected to be largest. Depending on the pattern shape, traction forces may be strongly localized leading to large displacements in very small areas. In this case, failure to track correctly a few beads in such areas would significantly alter the calculated force magnitude. Therefore, the pattern area is divided into smaller windows that are allowed to overlap, before applying the cross-correlation and tracking analysis. Reducing the size of the windows makes it possible to retrieve larger displacements with cross-correlation and, using overlapped windows, we can avoid missing beads close to the windows boundaries. Moreover, bead detection parameters are adjusted independently in the pattern area, since beads are usually less bright under the pattern due to photobleaching during UV irradiation. In this way, the inventors obtain a good tracking efficiency in the pattern region. Since the Fourier-transform traction cytometry (FTTC) method requires that the displacements should be known over a regular rectangular grid, they use a triangle-based linear interpolation to obtain such a field from the beads displacements. The grid spacing is chosen to be 0.72 μm in x and y directions.

All image processing and analysis were performed using Matlab. The part relative to particle localization and tracking is based on a Matlab package developed by Maria Kilfoil's group (Gao & Kilfoil (2009) *Optics Express* 17(6):4685-4704) (available at: www.physics.mcgill.ca/~kilfoil/downloads.html).

Traction Force Calculation

To calculate cell-induced traction stress from displacement data, the inventors have used the following assumptions: the substrate is supposed to exhibit a linear elastic behavior and, since the film thickness is large compared to typical displacements and adhesion sizes, it can be approximated as an elastic isotropic half-space so that the Boussinesq Green solution can be applied. Moreover, traction forces are assumed to be tangential to the plane of the substrate. In this case, given an incompressible gel (Poisson ratio close to 0.5), there is no out of plane displacement and the whole problem is two-dimensional. The stress field (local force per unit area) F(r) and the displacement field u(r) are related by:

$$u_i(r)=\int dr' G_{ij}(r-r')F(r')$$

in which implicit summation are applied with i,j=1,2 for two dimensions. $G_{ij}$ is the Boussinesq Green function. To solve the inverse problem of calculating forces from displacements, we applied the Fourier-transform traction cytometry (FTTC) method (Butler et al (2002) *Am J Physiol Cell Physiol* 282 (3):C595-605). The integral is approximated on a discrete computational mesh and the FTTC method takes advantage of the fact that the resulting system of linear equations can be solved more easily in Fourier space where the convolution becomes a simple product. Compared to algorithms that consist in inverting the system of equations in real space, FTTC is computationally much faster and easier to implement, while providing comparable results (Sabass et al, supra). Unlike the original work from Butler et al., the inventors used a zero order Tikhonov regularization scheme since the solution of the inverse problem is very sensitive to noise in the displacement data, leading to erratic behavior. Zero-order regularization consists in minimizing $\{|GF-u|^2+\lambda^2|F|^2\}$ where a side constraint is added that limits the amplitude of the forces. The regularization parameter $\lambda$ governs the relative importance between the two terms: whether the solution should be in better agreement with displacement data or more regularized. In practice, the inventors perform regularization directly in Fourier space (Sabass et al, supra) using the following expression for each wave vector k of the mesh:

$$\tilde{F}(k)=[{}^t\tilde{G}(k)\tilde{G}(k)+\lambda^2 I]^{-1}\tilde{G}(k)\tilde{F}(k)$$

where $\vec{F}$ and $\vec{u}$ are the 2D Fourier transform of the stress and displacement vectors, $\tilde{G}$ is the Fourier transform of the 2D Boussinesq Green function and I is the 2-by-2 identity matrix. A final inverse Fourier transformation is then performed to recover the stress field in real space. The regularization parameter $\lambda$ was adjusted to the lowest value which allows a reasonable solution to be computed. Increasing the regularization parameter has the effect of smoothing out the high spatial frequencies in the stress field. The inventors kept $\lambda$ at small values ($\lambda<\sim 10^{-9}$) in order to maintain the best spatial resolution, which is estimated to be about 5 µm in the present case.

Traction fields induced by cells on equivalent adhesive patterns can be averaged to yield statistically relevant results. Before averaging the calculated stress fields, it is preferable to correct for translation shifts between the images. To this avail, the inventors use the pattern fluorescence images (fibronectin) which are cross-correlated to determine their relative shift. The series of stress images are then aligned according to this criterion before being averaged.

Cell Culture
MCF10A Culture

The culture of MCF10A cells and the generation of $\Delta$CK2$\beta$ cell line was described previously (Deshiere et al (2008) *Mol Cell Biochem* 316(1-2):107-113). The MCF10A cell expressing ligand inducible Erb2 receptors were obtained from Ariad Pharmaceuticals (Muthuswamy et al (2001) *Nat Cell Biol* 3(9):785-792). Cells were seeded on micro-patterned substrate at a density of $8\times 10^4/cm^2$. Cells not attaching to the adhesive region on the substrate were washed away 1~2 hours after seeding. All the traction force measurement were performed 6 hours after seeding to ensure full spreading of cell. Substrate relaxation was assessed by detaching cells with trypsin.

To induce Erb2 cell line, AP 1510 (Ariad Pharmaceuticals) was added to the culture medium to a final concentration of 1 µM, 48 hr before traction force measurement.

TGF$\beta$ (R&D systems) was added at 2 ng/mL to the culture medium during 48 hr before cell plating on micropatterned PAA and traction force measurement.

Blebbistatin(-) (Sigma) at 100 µM was added progressively to the observation chamber to gradually obtain specific final concentration for the drug dose-response experiment. While for the time response experiment, Blebbistatin was added to directly reach a final concentration of 100 µM. Image acquisition started directly after the drug addition.

Fixation and Immuno-Stainings

Six hours after seeding on micropatterned gel or glass coverslip, cells were first extracted in cytoskeleton buffer (10 mM MES, 138 mM Kcl, 3 mM MgCl, 2 mM EGTA, pH6.1) containing 0.5% TritonX-100, then fixed in 4% paraformaldehyde. Fixed samples were wash 3 times in PBS. Afterward, samples were incubated for 1 hour in PBS containing 0.1% Tween, 3% BSA, and 10 µM Phalloidin-FITC (Sigma) to stain actin filaments. On glass cells were immuno labelled with primary antibodies directed against paxilin (BD Tranduction Laboratories) followed by immuno-labelling with secondary Cy3-labelled antibodies (Jackson Immuno Research). All coverslips were stained with Hoechst 33342 (Sigma) to reveal and count cell nuclei. After PBS washing, coverslips were mounted in Mowiol mounting medium.

Microscopy and Image Processing

Images of fixed cells were taken with a 100× objective (NA=1,35) on an Olympus BX-61 straight microscope, mounted with CDD camera (HQ2, Ropper Scientific) and driven with Metamorph (Molecular Devices). Live Imaging of beads displacement and micropattern deformation were performed with a 63× objective (NA=1,4) on an inverted 200M Zeiss microscope, mounted with CDD camera (HQ2, Ropper Scientific) and driven with Metamorph (Molecular Devices). Temperature and CO2 control were ensured by the Cube and the Box from LIS Imaging.

All the acquired images were processed by ImageJ (http://rsb.info.nih.gov/ij/). Averaged fluorescent staining images were automatically aligned using micropattern images by a custom written plugins. Pattern detection and length measurement were done automatically by custom written macro routines.

The invention claimed is:
1. A method for measuring a global cellular traction force of one or more cells, the method comprising:
   providing a soft substrate having disposed thereon a convex envelope of one or more adhesive micropattern(s), wherein:
   each adhesive micropattern has a size so as only one animal or human cell can adhere on said micropattern;
   each adhesive micropattern has a form suitable to concentrate the cellular traction force on one single region or one single point of said adhesive micropattern;
   each adhesive micropattern comprises a non-adhesive area and an adhesive area, said adhesive area comprising an adhesive spreading area and two sets of two adhesive spots, wherein:
   a) the adhesive spots are on or close to the convex envelope of the adhesive micropattern;
   b) each set contains a spot on either side of an axis in the plane of the convex envelope;

c) the two spots located on same side of the axis are separated by a non-adhesive region forming between 15% and 35% of the total length of the convex envelope;
d) the first set of adhesive spots is essentially located close to or on the axis in order to form an adhesive region of no more than 10% of the total length of the convex envelope; and
e) the adhesive spreading area is disposed on each side of the axis between the second set of adhesive spots to connect the two spots and toward the first set of adhesive spots between the two non-adhesive regions of c), exposing the substrate to at least one cell for a period of time sufficient to allow the cell(s) to bind to the adhesive micropattern;

measuring the position of said single region or said single point of said micropattern;

calculating the displacement of said single region or said single point of said micropattern, and determining the global cell traction force from said displacement of said single region or said single point of said micropattern.

2. The method of claim 1, wherein the global cellular traction force is determined from a calibration curve showing the relationship between the global cellular traction force and the displacement of said single region or single point of said micropattern.

3. The method of claim 1, wherein the adhesive micropattern has a form selected from the group consisting of the geometrical forms shown in FIG. 1B.

4. The method of claim 3, wherein the adhesive micropattern has a shape of crossbow.

5. The method of claim 1, wherein the single region or point is labelled.

6. The method of claim 1, wherein the substrate comprises several adhesive micropatterns, identical or different.

7. The method of claim 1, wherein the soft substrate is a polyacrylamide gel.

8. The method of claim 1, wherein the soft substrate has a Young's modulus of about 1 to about 10 kPa.

9. A method for determining the effect of a candidate/test molecule on the traction force of a cell, comprising:
measuring the traction force of a cell by the method of claim 1;
measuring the traction force of the cell incubating with the candidate/test molecule by the method of claim 1; and
comparing the traction force of the cell incubating with the candidate/test molecule with the traction force of the cell not incubating with the candidate/test molecule, thereby determining the effect of the candidate/test molecule on the traction force of the cell.

10. A method for determining the difference of cellular traction of two types of cells, comprising:

measuring the traction force of a first type of cells by the method of claim 1;
measuring the traction force of a second type of cells by the method of claim 1; and,
comparing the traction force of the first type of cells and that of the second type of cells, thereby determining the difference of cellular traction of the two types of cells.

11. A method for measuring a global cellular traction force of one or more cells, the method comprising:
providing a soft substrate having disposed thereon a convex envelope of one or more adhesive micropattern(s), wherein:
the convex envelope of the adhesive micropattern comprises an adhesive spreading area, and a non-adhesive area,
the adhesive micropattern further comprises a first set and a second set of adhesive spots, wherein each set of adhesive spots contains a spot on either side of an axis in the plane of the convex envelope; the surface between two of said spots located on the same side of the axis is a non-adhesive area; and the adhesive spots of said first set are located close to, or on, the axis, exposing the substrate to at least one cell for a period of time sufficient to allow the cell(s) to bind to the adhesive micropattern, measuring the position of said single region or said single point of said micropattern;

calculating the displacement of said single region or said single point of said micropattern, and determining the global cell traction force from said displacement of said single region or said single point of said micropattern.

12. The method of claim 11, wherein the adhesive spots of the first set are merged.

13. The method of claim 11, wherein the second set of adhesive spots is contained in the adhesive spreading area.

14. The method of claim 11, wherein the adhesive micropattern has a symmetry axis, said axis including the single point or the single region concentrating the cellular traction force.

15. The method of claim 1 wherein the adhesive micropattern comprises molecules promoting cell attachment which are selected from the group consisting of antigens, antibodies, cadherin, extracellular matrix molecules, synthetic peptides, and carbohydrates.

16. The method of claim 15, wherein the molecules promoting cell attachment are fluorescently labeled.

17. The method of claim 1, wherein displacement of said single region or said single point of said micropattern is the sole displacement which is calculated in order to determine the global cellular traction force.

* * * * *

UNITED STATES PATENT AND TRADEMARK OFFICE
CERTIFICATE OF CORRECTION

PATENT NO. : 9,250,241 B2
APPLICATION NO. : 13/984123
DATED : February 2, 2016
INVENTOR(S) : Manuel Thery and Qingzong Tseng It is certified that error appears in the above-identified patent and that said Letters Patent is hereby corrected as shown below:

In the Specification

Column 23,
Line 33,

" $\vec{F}(k) = \left[ {}^t \tilde{G}(k) \tilde{G}(k) + \lambda^2 I \right]^{-1} \tilde{G}(k) \vec{u}(k)$ ,, should read -- $\vec{\tilde{F}}(k) = \left[ {}^t \widetilde{G}(k) \widetilde{G}(k) + \lambda^2 I \right]^{-1} \widetilde{G}(k) \vec{\tilde{u}}(k)$ --.

Signed and Sealed this
Twenty-sixth Day of July, 2016

Michelle K. Lee
*Director of the United States Patent and Trademark Office*